US010357373B2

(12) United States Patent
Gargac et al.

(10) Patent No.: US 10,357,373 B2
(45) Date of Patent: Jul. 23, 2019

(54) REVERSE SHOULDER SYSTEMS AND METHODS

(71) Applicant: Tornier, Inc., Bloomington, MN (US)

(72) Inventors: Shawn M. Gargac, Fort Wayne, IN (US); Brian C. Hodorek, Winona Lake, IN (US); William Matthew Kuester, St. Louis Park, MN (US); Austin Wyatt Mutchler, Warsaw, IN (US)

(73) Assignee: Tornier, Inc., Bloomington, MN (US)

( * ) Notice: Subject to any disclaimer, the term of this patent is extended or adjusted under 35 U.S.C. 154(b) by 0 days.

(21) Appl. No.: 15/474,864

(22) Filed: Mar. 30, 2017

(65) Prior Publication Data

US 2018/0078377 A1    Mar. 22, 2018

Related U.S. Application Data

(63) Continuation of application No. 14/794,544, filed on Jul. 8, 2015, now Pat. No. 9,629,725, which is a
(Continued)

(51) Int. Cl.
*A61F 2/40* (2006.01)
*A61F 2/30* (2006.01)
(Continued)

(52) U.S. Cl.
CPC ........ *A61F 2/4081* (2013.01); *A61B 17/8033* (2013.01); *A61B 17/8052* (2013.01);
(Continued)

(58) Field of Classification Search
CPC .. A61F 2/40; A61F 2/4081; A61F 2002/4085; A61F 2002/4092;
(Continued)

(56) References Cited

U.S. PATENT DOCUMENTS 4,986,833 A    1/1991   Worland
5,033,036 A    7/1991   Ohmori et al.
(Continued)

FOREIGN PATENT DOCUMENTS

EP      0581667        2/1994
EP      1488764 B1     12/2006
(Continued)

OTHER PUBLICATIONS

EP Search Report and Written Opinion issued in European Patent Application No. 12153346.7, dated Mar. 8, 2012, in 6 pages.
(Continued)

*Primary Examiner* — Alvin J Stewart
(74) *Attorney, Agent, or Firm* — Knobbe Martens Olson & Bear LLP

(57) ABSTRACT

Reversed glenoid implants, and related kits and methods, are described that include an anchor member having a proximal head and a baseplate having a distal end with a first aperture sized to accept the proximal head of the anchor member. The proximal head is inserted along an un-threaded length thereof from the distal end into the first aperture, and the anchor member is restrained against axial translation with respect to the baseplate but is permitted to rotate with respect to the baseplate.

31 Claims, 33 Drawing Sheets

Related U.S. Application Data continuation-in-part of application No. PCT/US2014/072442, filed on Dec. 26, 2014.

(60) Provisional application No. 61/923,382, filed on Jan. 3, 2014.

(51) Int. Cl.
  *A61B 17/80* (2006.01)
  *A61B 17/86* (2006.01)

(52) U.S. Cl.
  CPC ........... *A61B 17/86* (2013.01); *A61F 2/30749* (2013.01); *A61F 2002/305* (2013.01); *A61F 2002/30013* (2013.01); *A61F 2002/3085* (2013.01); *A61F 2002/30332* (2013.01); *A61F 2002/30367* (2013.01); *A61F 2002/30405* (2013.01); *A61F 2002/30497* (2013.01); *A61F 2002/30507* (2013.01); *A61F 2002/30538* (2013.01); *A61F 2002/30571* (2013.01); *A61F 2002/30607* (2013.01); *A61F 2002/30774* (2013.01); *A61F 2002/30787* (2013.01); *A61F 2002/4085* (2013.01)

(58) Field of Classification Search
  CPC .......... A61F 2/4059; A61F 2002/30364; A61F 2002/30369; A61F 2002/30365
  See application file for complete search history.

(56) References Cited

U.S. PATENT DOCUMENTS

| | | | |
|---|---|---|---|
| 5,080,673 A | 1/1992 | Burkhead et al. | |
| 5,458,637 A | 10/1995 | Hayes | |
| 5,489,309 A | 2/1996 | Lackey et al. | |
| 5,489,311 A | 2/1996 | Cipolletti | |
| 5,531,973 A | 7/1996 | Sarv | |
| 5,800,551 A | 9/1998 | Williamson et al. | |
| 5,954,722 A | 9/1999 | Bono | |
| 6,102,954 A | 8/2000 | Albrektsson et al. | |
| 6,171,342 B1 | 1/2001 | O'Neil et al. | |
| 6,228,119 B1 | 5/2001 | Ondrla et al. | |
| 6,406,495 B1 | 6/2002 | Schoch | |
| 6,508,841 B2 | 1/2003 | Martin et al. | |
| 6,514,287 B2 | 2/2003 | Ondrla et al. | |
| 6,673,115 B2 | 1/2004 | Resch et al. | |
| 6,679,916 B1 | 1/2004 | Frankle et al. | |
| 6,699,289 B2 | 3/2004 | Iannotti et al. | |
| 6,761,740 B2 | 7/2004 | Tornier | |
| 6,790,234 B1 | 9/2004 | Frankle | |
| 6,860,903 B2 | 3/2005 | Mears et al. | |
| 6,953,478 B2 | 10/2005 | Bouttens et al. | |
| 7,169,184 B2 | 1/2007 | Pria | |
| 7,175,663 B1 | 2/2007 | Stone | |
| 7,175,665 B2 | 2/2007 | German et al. | |
| 7,204,854 B2 | 4/2007 | Guederian et al. | |
| 7,316,715 B2 | 1/2008 | Plaskon | |
| 7,462,197 B2 | 12/2008 | Tornier | |
| 7,462,199 B2 | 12/2008 | Justin et al. | |
| 7,604,665 B2 | 10/2009 | Iannotti et al. | |
| 7,608,109 B2 | 10/2009 | Pria | |
| 7,621,961 B2 | 11/2009 | Stone | |
| 7,637,928 B2 | 12/2009 | Fernandez | |
| 7,648,530 B2 | 1/2010 | Habermeyer et al. | |
| 7,666,522 B2 | 2/2010 | Justin et al. | |
| 7,753,959 B2 | 7/2010 | Berelsman et al. | |
| 7,766,969 B2* | 8/2010 | Justin | A61F 2/30749 623/20.15 |
| 7,854,768 B2 | 12/2010 | Wiley et al. | |
| 7,892,287 B2 | 2/2011 | Deffenbaugh | |
| 7,922,769 B2 | 4/2011 | Deffenbaugh et al. | |
| 7,927,335 B2 | 4/2011 | Deffenbaugh et al. | |
| 7,993,408 B2 | 8/2011 | Meridew et al. | |
| 8,007,523 B2 | 8/2011 | Wagner et al. | |
| 8,048,161 B2 | 11/2011 | Guederian et al. | |
| 8,062,376 B2 | 11/2011 | Shultz et al. | |
| 8,070,820 B2* | 12/2011 | Winslow | A61F 2/40 623/19.11 |
| 8,092,545 B2 | 1/2012 | Coon et al. | |
| 8,206,453 B2 | 6/2012 | Cooney, III et al. | |
| 8,231,683 B2 | 7/2012 | Lappin et al. | |
| 8,241,365 B2 | 8/2012 | Williams, Jr. et al. | |
| 8,287,600 B2 | 10/2012 | Angibaud | |
| 8,308,807 B2 | 11/2012 | Seebeck et al. | |
| 8,357,201 B2 | 1/2013 | Mayer et al. | |
| 8,361,157 B2 | 1/2013 | Bouttens et al. | |
| 8,425,614 B2 | 4/2013 | Winslow et al. | |
| 8,444,680 B2 | 5/2013 | Dooney, Jr. et al. | |
| 8,449,617 B1 | 5/2013 | McDaniel et al. | |
| 8,454,702 B2 | 6/2013 | Smits et al. | |
| 8,465,548 B2 | 6/2013 | Long | |
| 8,480,750 B2 | 7/2013 | Long | |
| 8,532,806 B1 | 9/2013 | Masson | |
| 8,556,902 B2 | 10/2013 | Ek et al. | |
| 8,556,980 B2 | 10/2013 | Deffenbaugh | |
| 8,556,981 B2 | 10/2013 | Jones et al. | |
| 8,591,591 B2 | 11/2013 | Winslow et al. | |
| 8,597,334 B2 | 12/2013 | Mocanu | |
| 8,632,597 B2 | 1/2014 | Lappin | |
| 8,690,951 B2 | 4/2014 | Baum et al. | |
| 8,753,402 B2 | 6/2014 | Winslow et al. | |
| 8,790,402 B2 | 7/2014 | Monaghan et al. | |
| 8,840,676 B2 | 9/2014 | Belew | |
| 8,864,834 B2 | 10/2014 | Boileau et al. | |
| 8,961,611 B2 | 2/2015 | Long | |
| 9,114,017 B2 | 8/2015 | Lappin | |
| 9,498,345 B2 | 11/2016 | Burkhead et al. | |
| 9,629,725 B2* | 4/2017 | Gargac | A61F 2/4081 |
| 10,064,734 B2 | 9/2018 | Burkhead et al. | |
| 2002/0095214 A1 | 7/2002 | Hyde, Jr. | |
| 2003/0149485 A1 | 8/2003 | Tornier | |
| 2004/0106928 A1 | 6/2004 | Ek | |
| 2004/0220673 A1 | 11/2004 | Pria | |
| 2004/0220674 A1 | 11/2004 | Pria | |
| 2005/0049709 A1 | 3/2005 | Tornier | |
| 2005/0143831 A1 | 6/2005 | Justin et al. | |
| 2005/0149044 A1 | 7/2005 | Justin et al. | |
| 2005/0261775 A1 | 11/2005 | Baum et al. | |
| 2005/0278030 A1 | 12/2005 | Tornier | |
| 2006/0074353 A1 | 4/2006 | Deffenbaugh et al. | |
| 2006/0100714 A1 | 5/2006 | Ensign | |
| 2006/0122705 A1 | 6/2006 | Morgan | |
| 2006/0142865 A1 | 6/2006 | Hyde, Jr. | |
| 2006/0200248 A1* | 9/2006 | Beguin | A61F 2/4081 623/19.11 |
| 2006/0200249 A1 | 9/2006 | Beguin et al. | |
| 2007/0016304 A1 | 1/2007 | Chudik | |
| 2007/0055380 A1 | 3/2007 | Berelsman et al. | |
| 2007/0100458 A1 | 5/2007 | Pria | |
| 2007/0142921 A1* | 6/2007 | Lewis | A61B 17/86 623/22.36 |
| 2007/0156246 A1 | 7/2007 | Meswania et al. | |
| 2007/0179624 A1 | 8/2007 | Stone et al. | |
| 2007/0219638 A1 | 9/2007 | Jones et al. | |
| 2007/0244563 A1 | 10/2007 | Roche et al. | |
| 2008/0269906 A1 | 10/2008 | Iannotti et al. | |
| 2008/0294268 A1 | 11/2008 | Baum et al. | |
| 2008/0306601 A1 | 12/2008 | Dreyfuss | |
| 2009/0149961 A1 | 6/2009 | Dallmann | |
| 2009/0204225 A1 | 8/2009 | Meridew et al. | |
| 2009/0216332 A1 | 8/2009 | Splieth et al. | |
| 2009/0281630 A1 | 11/2009 | Delince et al. | |
| 2010/0016975 A1 | 1/2010 | Iannotti et al. | |
| 2010/0023068 A1 | 1/2010 | Bouttens et al. | |
| 2010/0049327 A1 | 2/2010 | Isch et al. | |
| 2010/0087927 A1 | 4/2010 | Roche et al. | |
| 2010/0161066 A1 | 6/2010 | Iannotti et al. | |
| 2010/0217399 A1* | 8/2010 | Groh | A61F 2/4081 623/19.11 |
| 2010/0234959 A1 | 9/2010 | Roche et al. | |
| 2010/0274359 A1 | 10/2010 | Brunnarius et al. | |
| 2010/0291401 A1 | 11/2010 | Medina et al. | |
| 2010/0331990 A1 | 12/2010 | Mroczkowski | |

(56) References Cited

U.S. PATENT DOCUMENTS

| | | |
|---|---|---|
| 2011/0035013 A1 | 2/2011 | Winslow et al. |
| 2011/0118846 A1 | 5/2011 | Katrana et al. |
| 2011/0144760 A1 | 6/2011 | Wong et al. |
| 2011/0190899 A1 | 8/2011 | Pierce et al. |
| 2011/0282393 A1 | 11/2011 | Garlach et al. |
| 2012/0004733 A1 | 1/2012 | Hodorek et al. |
| 2012/0029647 A1 | 2/2012 | Winslow et al. |
| 2012/0165954 A1 | 6/2012 | Nimal |
| 2012/0191201 A1 | 7/2012 | Smits et al. |
| 2012/0209392 A1 | 8/2012 | Angibaud et al. |
| 2012/0221111 A1* | 8/2012 | Burkhead, Jr. ....... A61F 2/4081 623/19.11 |
| 2012/0221112 A1 | 8/2012 | Lappin |
| 2012/0232670 A1 | 9/2012 | Bojarski et al. |
| 2012/0239156 A1 | 9/2012 | De Wilde et al. |
| 2012/0253467 A1 | 10/2012 | Frankle |
| 2012/0277880 A1* | 11/2012 | Winslow ............... A61F 2/4081 623/19.11 |
| 2013/0018483 A1 | 1/2013 | Li et al. |
| 2013/0053968 A1 | 2/2013 | Nardini et al. |
| 2013/0096631 A1 | 4/2013 | Leung et al. |
| 2013/0110470 A1 | 5/2013 | Vanasse et al. |
| 2013/0150972 A1* | 6/2013 | Iannotti ................. A61F 2/4081 623/18.11 |
| 2013/0150973 A1* | 6/2013 | Splieth .................. A61F 2/4081 623/19.11 |
| 2013/0150975 A1 | 6/2013 | Iannotti et al. |
| 2013/0226309 A1 | 8/2013 | Daigo et al. |
| 2013/0231754 A1 | 9/2013 | Daigo et al. |
| 2013/0253656 A1 | 9/2013 | Long |
| 2013/0261751 A1 | 10/2013 | Lappin |
| 2013/0261752 A1 | 10/2013 | Lappin et al. |
| 2013/0264749 A1 | 10/2013 | Jones et al. |
| 2013/0282135 A1 | 10/2013 | Sun et al. |
| 2014/0025173 A1 | 1/2014 | Cardon et al. |
| 2014/0142711 A1 | 5/2014 | Maroney et al. |
| 2014/0194995 A1 | 7/2014 | Koka |
| 2014/0257499 A1 | 9/2014 | Winslow et al. |
| 2014/0277180 A1 | 9/2014 | Paolino et al. |
| 2014/0371863 A1 | 12/2014 | Vanasse et al. |
| 2015/0094819 A1 | 4/2015 | Iannotti et al. |
| 2015/0142122 A1 | 5/2015 | Bickley et al. |
| 2015/0150688 A1 | 6/2015 | Vanasse et al. |
| 2015/0272741 A1 | 10/2015 | Taylor et al. |
| 2015/0305877 A1 | 10/2015 | Gargac et al. |
| 2016/0270922 A1 | 9/2016 | Pressacco et al. |
| 2016/0287401 A1 | 10/2016 | Muir et al. |
| 2016/0310285 A1 | 10/2016 | Kovacs et al. |
| 2016/0324649 A1 | 11/2016 | Hodorek et al. |
| 2017/0042690 A1 | 2/2017 | Burkhead et al. |
| 2017/0172764 A1 | 6/2017 | Muir et al. |
| 2018/0243102 A1 | 8/2018 | Burkhead, Jr. et al. |

FOREIGN PATENT DOCUMENTS

| | | |
|---|---|---|
| EP | 1762201 A1 | 3/2007 |
| EP | 1515758 B1 | 3/2009 |
| EP | 1639966 B1 | 9/2009 |
| EP | 1927328 B1 | 1/2011 |
| EP | 1902689 B1 | 11/2011 |
| EP | 1996125 B1 | 5/2013 |
| EP | 2335655 B1 | 7/2013 |
| EP | 1951161 B1 | 4/2014 |
| EP | 1973498 B1 | 4/2014 |
| EP | 2481376 B1 | 4/2014 |
| FR | 2739151 A1 | 3/1997 |
| FR | 2776506 B1 | 8/2000 |
| FR | 2971144 A1 | 8/2012 |
| FR | 2977791 B1 | 7/2014 |
| WO | WO 2011/073169 | 6/2011 |
| WO | WO 2011/150180 A2 | 12/2011 |
| WO | WO 2015/068035 | 5/2015 |
| WO | WO 2015/103090 | 7/2015 |
| WO | WO 2017/007565 | 1/2017 |

OTHER PUBLICATIONS

French Search Report and Written Opinion issued in Application. No. FR1150994, dated May 27, 2011, in 7 pages.

International Search Report and Written Opinion issue in PCT Application No. PCT/US2014/072442, dated Mar. 11, 2015, in 13 pages.

International Search Report and Written Opinion issue in PCT Application No. PCT/US2016/036500, dated Mar. 22, 2017, in 18 pages.

Anatomical Shoulder™ Inverse/Reverse System Surgical Technique, Product Brochure, Zimmer, Inc., published 2006, in 32 pages.

Boileau, P., et al., "Cemented polyethylene versus uncemented metal-backed glenoid components in total shoulder arthroplasty: A prospective, double-blind, randomized study," Journal of Shoulder and Elbow Surgery, Jul./Aug. 2002, vol. 11, Issue 4, pp. 351-359.

Boileau, P., et al., "Metal-backed glenoid implant with polyethylene insert is not a viable long-term therapeutic option," Journal of Shoulder and Elbow Surgery, Feb. 2015, pp. 1-10.

Castagna, A., et al., "Mid-term results of a metal-backed glenoid component in total shoulder replacement," The Journal of Bone and Joint Surgery, Oct. 2010, vol. 92-B, No. 10, pp. 1410-1415.

Clement, N.D., et al., "An uncemented metal-backed glenoid component in total shoulder arthroplasty for osteoarthritis: factors affecting survival and outcome," The Japanese Orthopaedic Association, published online Sep. 26, 2012, vol. 18, pp. 22-28.

Eclipse™ Stemless Shoulder Prosthesis, Surgical Technique Guide, Anthrex GmbH, 2014, in 12 pages.

Epoca Shoulder Arthroplasty System, Synthes, Inc., Apr. 2008, in 4 pages.

Epoca Shoulder Arthroplasty System—Stem and Glenoid Technique Guide, Synthes, Inc., Apr. 2008, in 56 pages.

Extended European Search Report for EP Appl. No. 16161842.6 dated Sep. 30, 2016 in 7 pages.

Kany, J., et al., "A convertible shoulder system: is it useful in total shoulder arthroplasty revisions?" International Orthopaedics, published online Oct. 16, 2014, vol. 39, pp. 299-304.

Katz, D., et al., "New design of a cementless glenoid component in unconstrained shoulder arthroplasty: a prospective medium-term analysis of 143 cases," published online Oct. 27, 2012, vol. 23, pp. 27-34.

Montoya, F., et al., "Midterm results of a total shoulder prosthesis fixed with a cementless glenoid component," Journal of Shoulder and Elbow Surgery, May 2013, vol. 22, Issue 5, pp. 628-635.

SMR Axioma® TT Metal Back Surgical Technique, Product Brochure, Lima Corporate, dated Sep. 2013, in 48 pages.

Taunton, M.J., et al., "Total Shoulder Arthroplasty with a Metal-Backed, Bone-Ingrowth Glenoid Component," The Journal of Bone and Joint Surgery, Oct. 2008, vol. 90-A, Issue 10, pp. 2180-2188.

Teissier, P., et al., "The TESS reverse shoulder arthroplasty without a stem in the treatment of cuff-deficient shoulder conditions: clinical and radiographic results," Journal of Shoulder and Elbow Surgery, Jan. 2015, vol. 24, Issue 1, pp. 45-51.

The Anatomical Shoulder™: A true system approach, Product Brochure, Zimmer UK Ltd, printed 2006, in 6 pages.

Univers Revers™ Total Shoulder System, Surgical Technique Guide, Anthrex Inc., Version D, revised Jul. 2, 2015, in 28 pages.

* cited by examiner

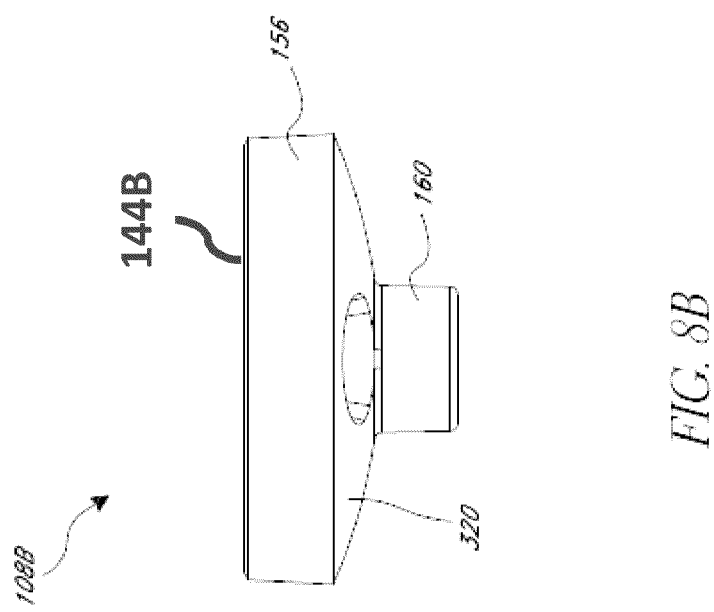

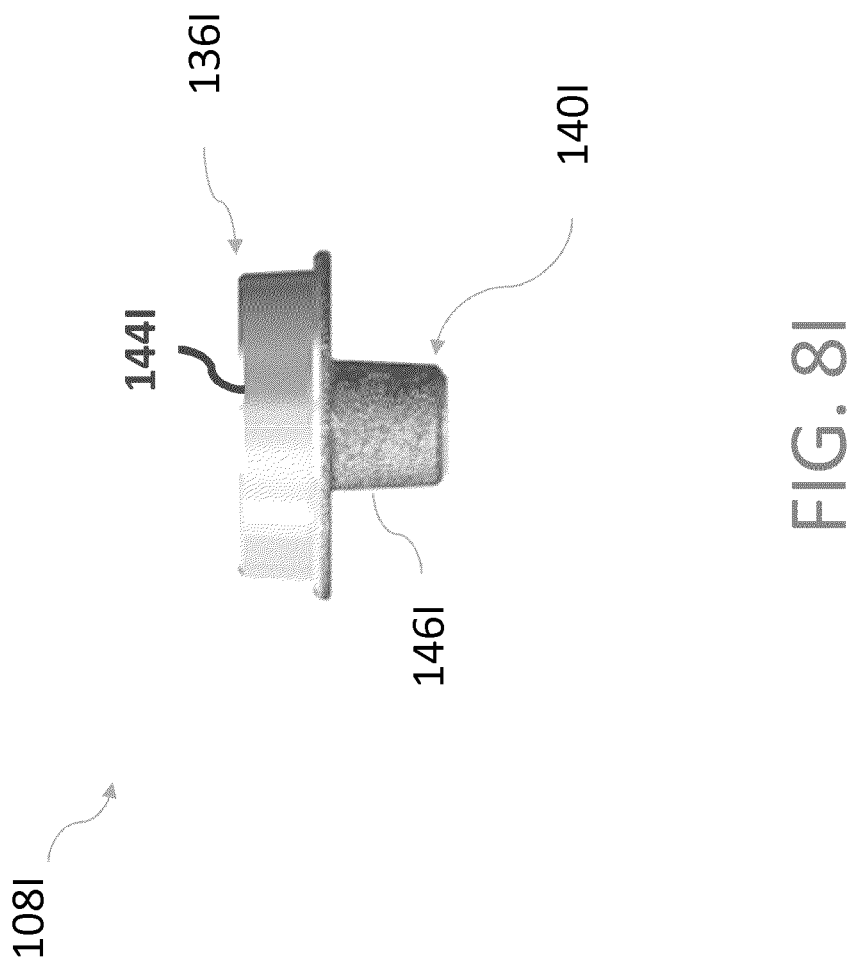

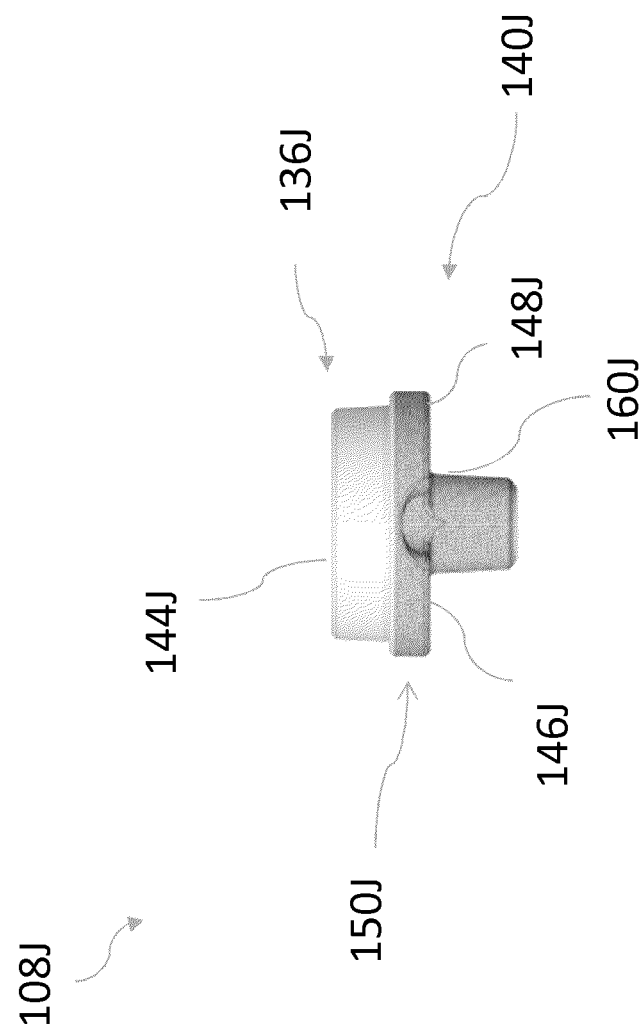

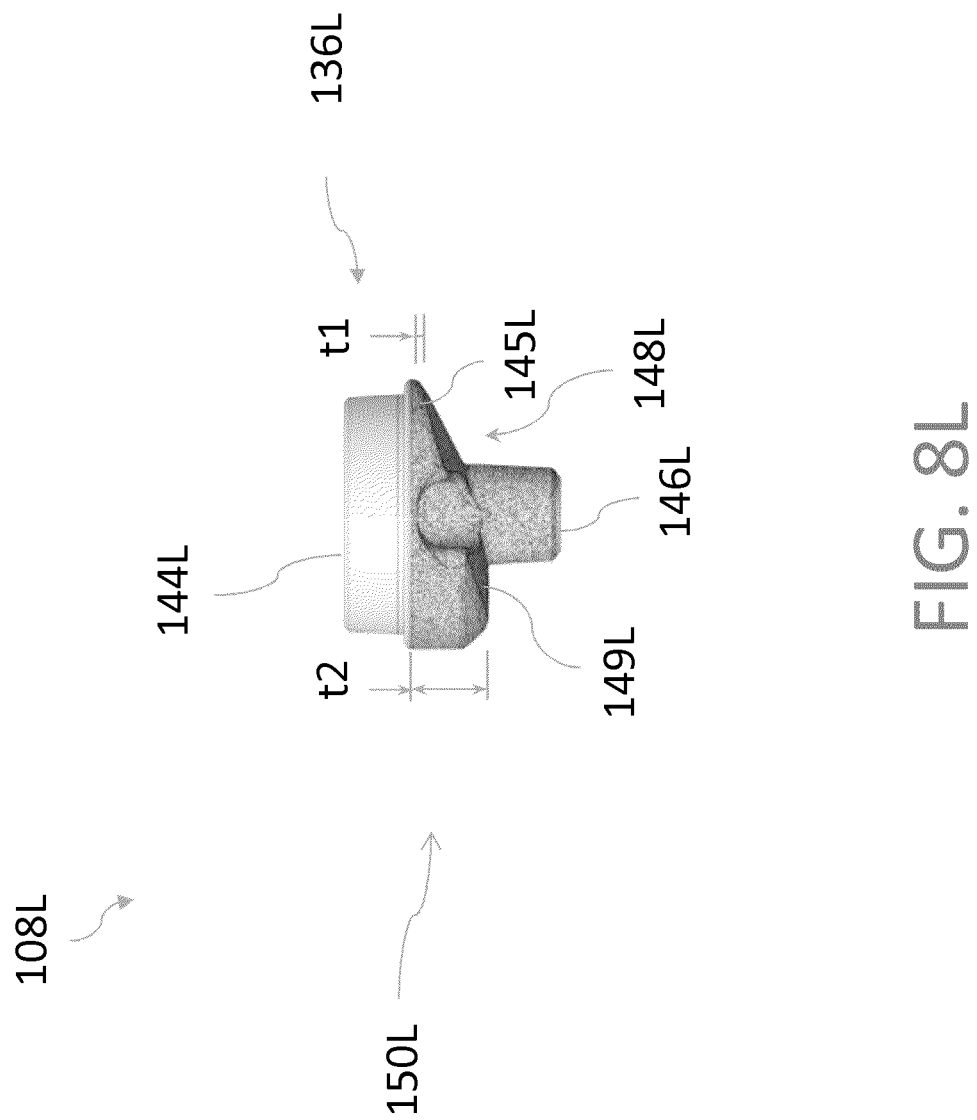

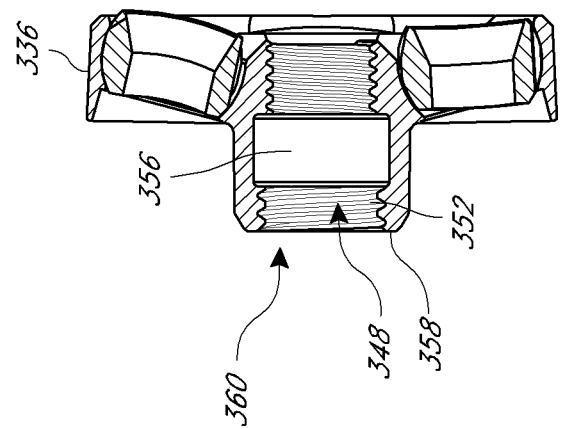
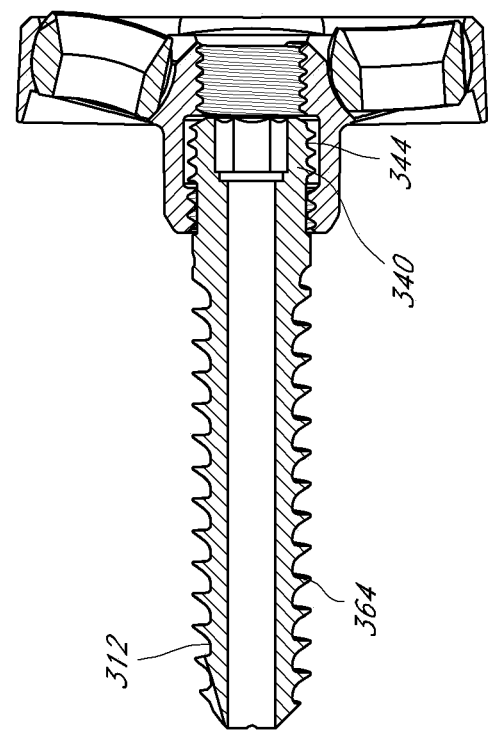
FIG. 9B
FIG. 9A

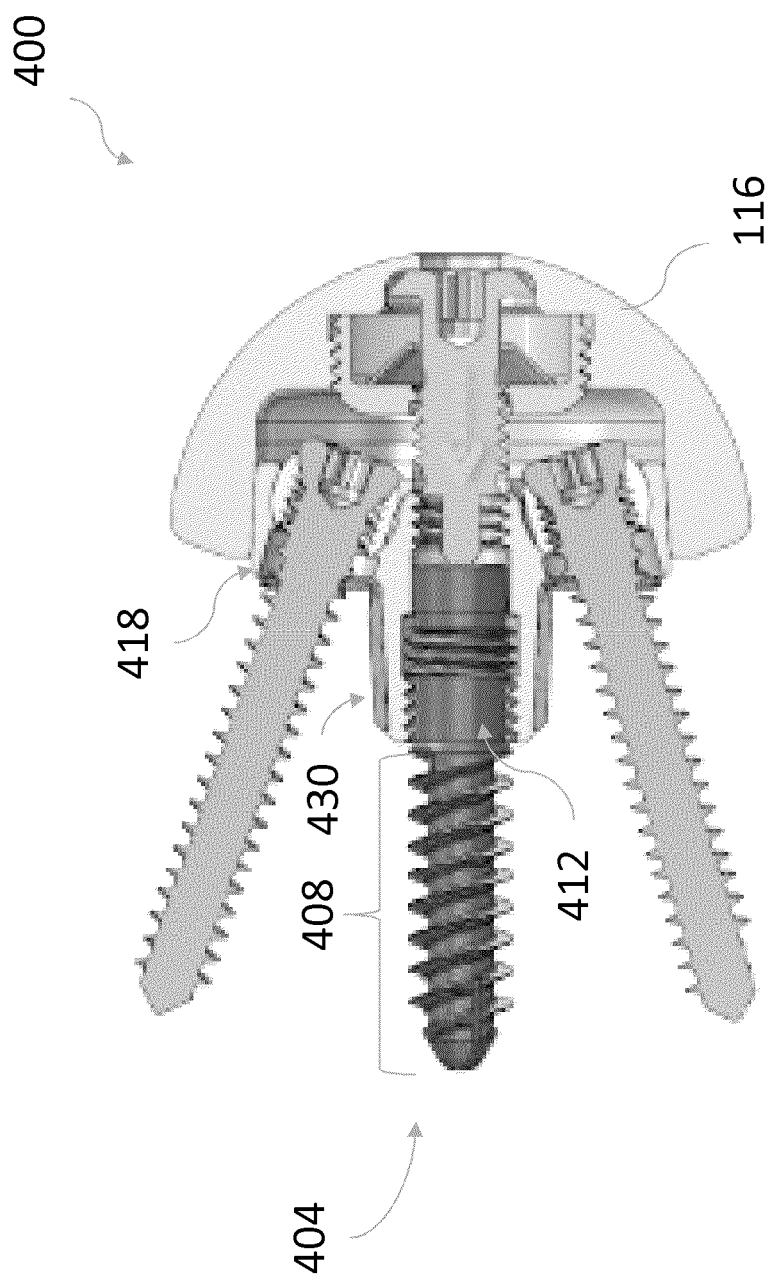

REVERSE SHOULDER SYSTEMS AND METHODS

INCORPORATION BY REFERENCE TO ANY PRIORITY APPLICATIONS

The present application is a continuation of U.S. application Ser. No. 14/794,544, filed Jul. 8, 2015, which is a continuation-in-part of PCT Application No. PCT/US2014/072442, filed Dec. 26, 2014, which claims the priority benefit of U.S. Provisional Application No. 61/923,382, filed Jan. 3, 2014. Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

The systems and methods described herein are directed to orthopedic implants, for example to reverse shoulder replacement systems and methods for implantation.

Description of the Related Art

Shoulder replacement surgery involves placing a motion providing device at the glenohumeral joint, i.e., the joint interface between the scapula and the proximal humerus of the arm. See FIG. 1. Reverse shoulder replacement reverses the curvature of the natural glenoid cavity and the proximal head of the humerus. That is, a convex surface of a glenoid component is positioned on the scapula and a concave surface of a humeral component is positioned on the proximal humerus.

Some reverse shoulder systems have limitations in connection with the fixation of the glenoid component. In some glenoid component designs, a one-piece construct is provided in which a central threaded post projects from a baseplate. The threaded post provides fixation to the bone of the scapula, but provides little to no flexibility of the final positioning of peripheral features of the baseplate, such as screw or mount holes thereon. Also, the unitary nature of this approach requires more inventory to provide a proper mix of baseplate configurations and threaded post sizes.

Other reverse shoulder systems provide a plate having an integral fixed central post and a plurality of screws that are placed through either the post or the plate. These systems are limited in that the length, inner diameter, and configuration of the central post are fixed. As such, the size of a screw placed through the central post is predefined which limits the ability to perform revisions (subsequent surgeries on the patient to replace the system). In a revision surgery the old implant must be removed and replaced with a new implant. Commonly a substantial amount of bone is removed with the old implant and in this case larger screws are required to securely fix the new glenoid implant to the scapula.

In currently available systems, specifically unitary systems having an integral fixed central threaded post, independent rotation is not provided between the post and the baseplate. For these unitary systems the post and the baseplate rotate together when the post is driven into the bone. With other glenoid implants wherein an anchor member is driven through the baseplate and extends from a distal end of the baseplate, axial translation of the baseplate relative to the anchor member is not prevented. For these systems, the baseplate is not secured against axial translation until the anchor member is fully engaged in the scapula and pulls the baseplate against the surface of the bone thereby preventing rotation of the baseplate.

SUMMARY OF THE INVENTION

There is a need for new shoulder prosthesis systems that can provide more flexibility and better adaptability to patient anatomies while maximizing revision options. When implanting reverse shoulder systems it is desirable to independently attach a baseplate to the scapula and thereafter to independently rotate the baseplate with respect to the scapula such that fixation means in the periphery of the baseplate can be driven into bone thereunder.

A glenoid implant, according to some embodiments disclosed herein, includes an anchor member and a baseplate. The anchor member has a longitudinal portion configured to be secured to a bone and a proximal head. The proximal head has a first engaging surface. The baseplate has a proximal end and a distal end. The distal end of the baseplate comprises a first aperture sized to accept the proximal head of the anchor member and a second engaging surface. When the proximal head is inserted from the distal end of the baseplate into the first aperture, the first engaging surface couples with the second engaging surface. In some embodiments, the anchor member is restrained against axial translation by this engagement with respect to the baseplate but is permitted to rotate with respect to the baseplate.

Other embodiments of a glenoid implant may further comprise a locking structure configured to apply a force to the anchor member. A glenoid implant may further comprise a glenosphere configured to be attached to the baseplate. A glenoid implant may also include one or more perimeter anchors for securing the baseplate to bone.

A method for implanting a glenoid implant, according to some embodiments disclosed herein, includes providing an anchor member and a baseplate. The anchor member has a longitudinal portion configured to be secured to a bone and a proximal head. The proximal head has a first engaging surface. The baseplate has a proximal end and a distal end. The distal end of the baseplate comprises a first aperture sized to accept the proximal head of the anchor member and a second engaging surface. The method includes securing the anchor member at least partially to bone. The method further includes, with the proximal head of the anchor member inserted into the first aperture such that the first engaging surface is coupled to the second engaging surface, rotating the baseplate relative to the anchor member to adjust the position of the baseplate without adjusting the rotational position of the anchor member. The method may further include securing the baseplate to the bone.

In some embodiments, a method further comprises, prior to securing the anchor member at least partially to bone, inserting the proximal head into the first aperture to cause the first engaging surface to couple with the second engaging surface. A method may also comprise applying a force to the anchor member with a locking member to prevent rotation between the anchor member and the baseplate. A method may also comprise engaging a glenosphere to the baseplate. In some embodiments, securing the baseplate to bone comprises inserting one or more perimeter anchors through one or more openings in the baseplate.

Other embodiments of the invention include additional implants or components of implants, as well as further methods, described herein. A system or kit may also be provided according to some embodiments, wherein the system or kit comprises a plurality of anchor members engageable with one or more baseplates and/or a plurality of baseplates engageable with one or more anchor members, examples of which are described further herein.

In other embodiments, a glenoid implant for a shoulder prosthesis is formed. The glenoid implant comprises an anchor member and a baseplate. The anchor member has a longitudinal portion configured to be secured to a bone and a proximal head. The proximal head has an external threaded surface. The baseplate has a proximal end and a distal end. The distal end has a first aperture sized to accept the proximal head of the anchor member. The first aperture has an internal threaded surface and a space disposed proximal of the internal threaded surface. When the external threaded surface of the proximal head is disposed proximal of the internal threaded surface of the first aperture, the anchor member is restrained against axial translation with respect to the baseplate but is rotatable with respect to the anchor member.

In another embodiment, a glenoid implant for a shoulder prosthesis is provided that includes a baseplate, an internal member, and a screw. The baseplate has a proximal end, a distal end, an outer periphery, and an aperture that extends therethrough adjacent to the outer periphery. The aperture extends from the proximal end to a bone engaging surface. The internal member disposed in the baseplate has an internal threaded surface surrounding the aperture. The screw is configured to be placed through the aperture. The screw has an external threaded surface. A first number of thread starts disposed on the internal threaded surface of the internal member is greater than a second number of thread starts disposed on the external threaded surface of the screw. The threads of the external threaded surface of the anchor member have a constant thread form along the length thereof.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of each of the drawings.

FIGS. 8B-8E are side views of different embodiments of baseplates.

FIG. 8I is a side view of a baseplate with a distal portion formed by additive manufacturing.

FIG. 8J is a side view of a lateralized baseplate formed by additive manufacturing.

FIG. 8L is a full-wedge baseplate formed by additive manufacturing.

FIG. 9A is a cross-sectional side view of a baseplate with a dual threaded lumen and an anchor member.

FIG. 9B is a cross-sectional side view of the baseplate of FIG. 9A.

FIG. 9C is a cross-sectional side view of a glenoid implant with a baseplate that has a dual threaded lumen and an anchor member.

FIG. 9I is a side cross-sectional view of a proximal portion of the peripheral screw of FIG. 9H partially advanced through the internal member of FIG. 9G.

DETAILED DESCRIPTION OF THE PREFERRED EMBODIMENTS

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Figure 1:
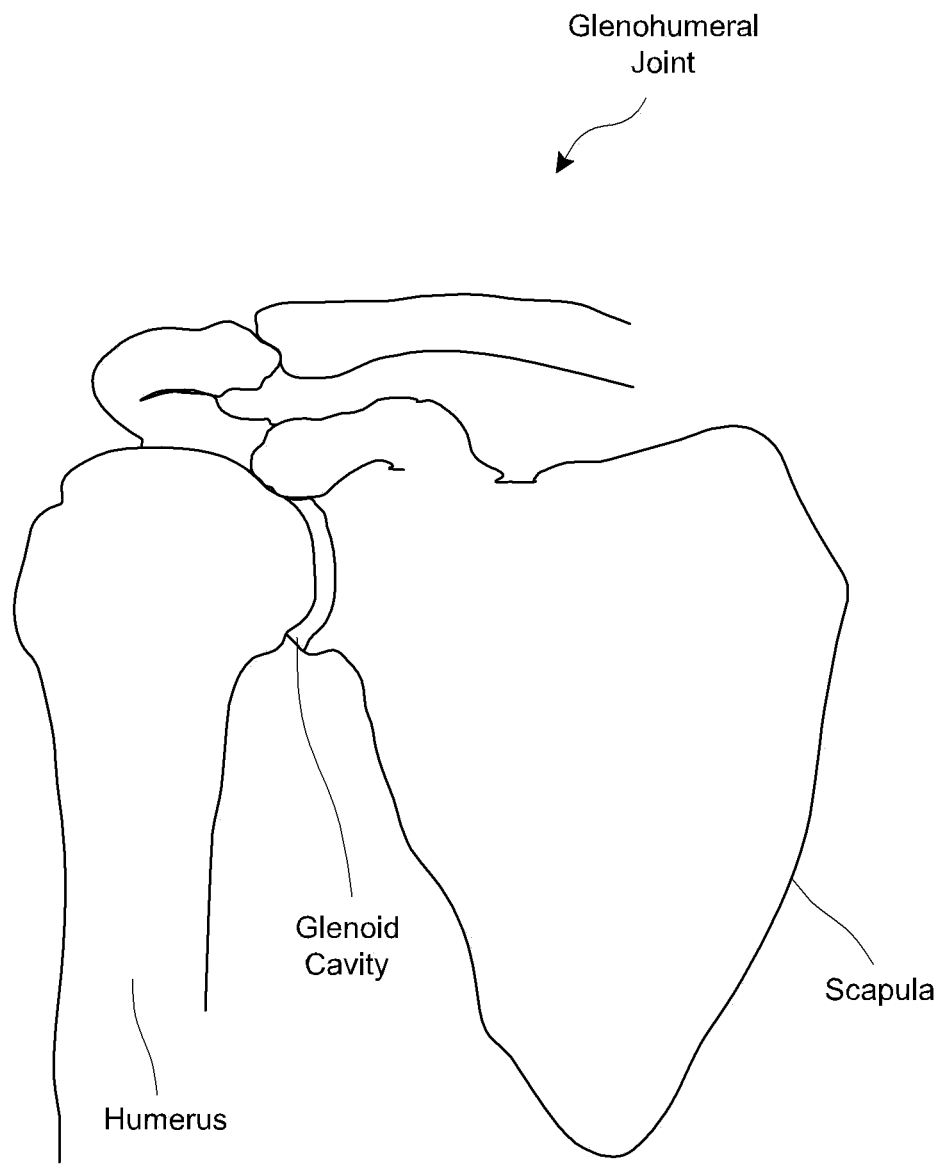
FIG. 1 is a schematic view of the human shoulder.

FIG. 1 depicts the human shoulder. The glenoid cavity is a portion of the shoulder that is located on the scapula. The glenoid cavity articulates with the head of the humerus to permit motion of the glenohumeral joint. Total shoulder arthroplasty replaces the glenohumeral joint with prosthetic articular surfaces that replicate the naturally occurring concave and convex surfaces of the body. Typically, in total shoulder arthroplasty, an articular surface replaces the humeral head and an articular surface replaces cartilage in the glenoid cavity. In a typical reverse total shoulder arthroplasty, a glenoid implant with a convex spherical head is inserted into the glenoid cavity and a complimentary socket is placed on the humerus. Reverse total shoulder arthroplasty reverses the naturally occurring ball and socket orientation related to the glenohumeral joint.

Figure 2:
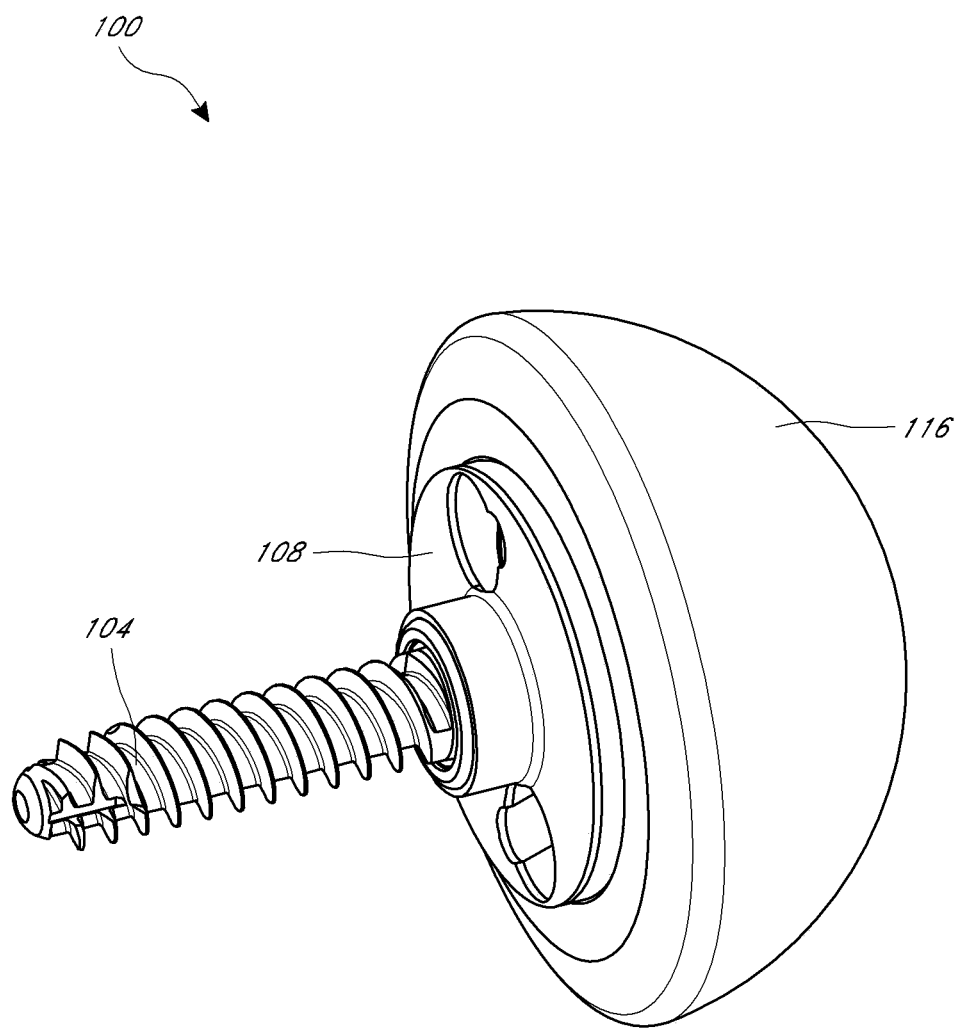
FIG. 2 is a perspective view of a glenoid implant in an assembled configuration.
Figure 3:
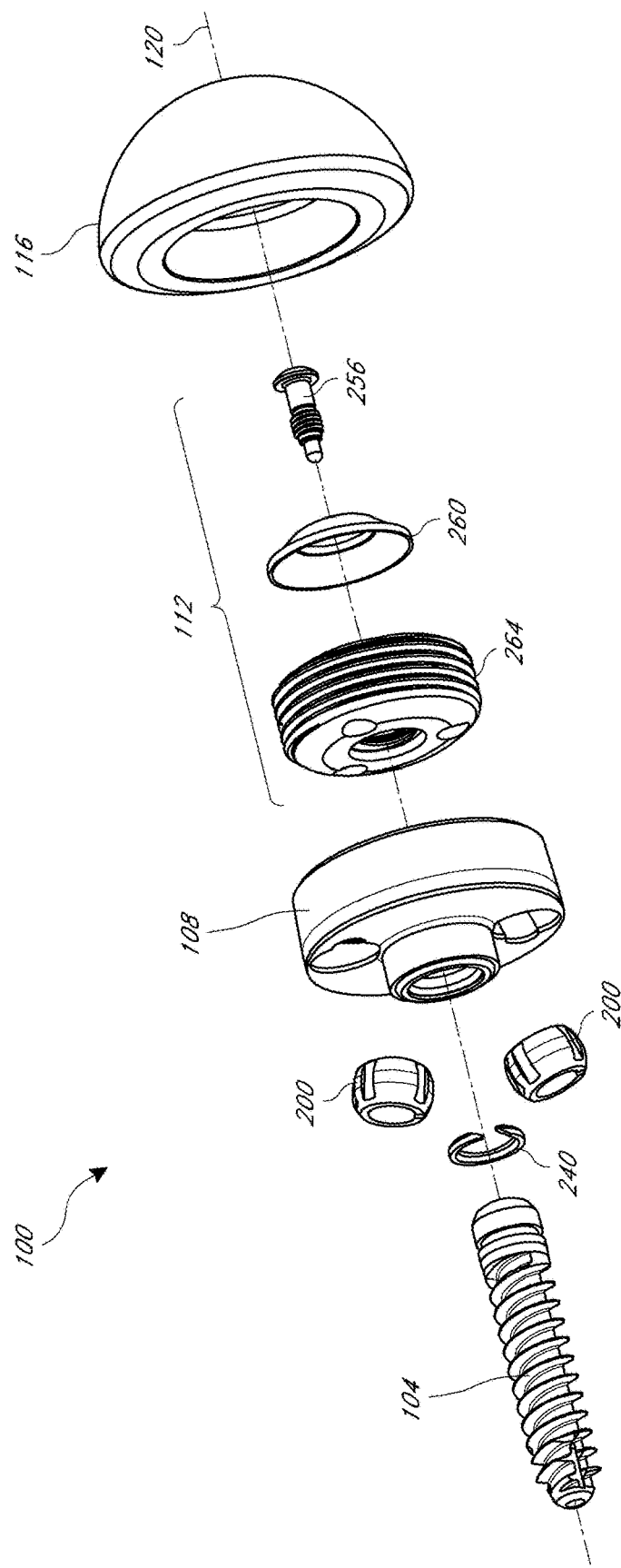
FIG. 3 is an exploded view of the glenoid implant shown in FIG. 2.
Figure 4:
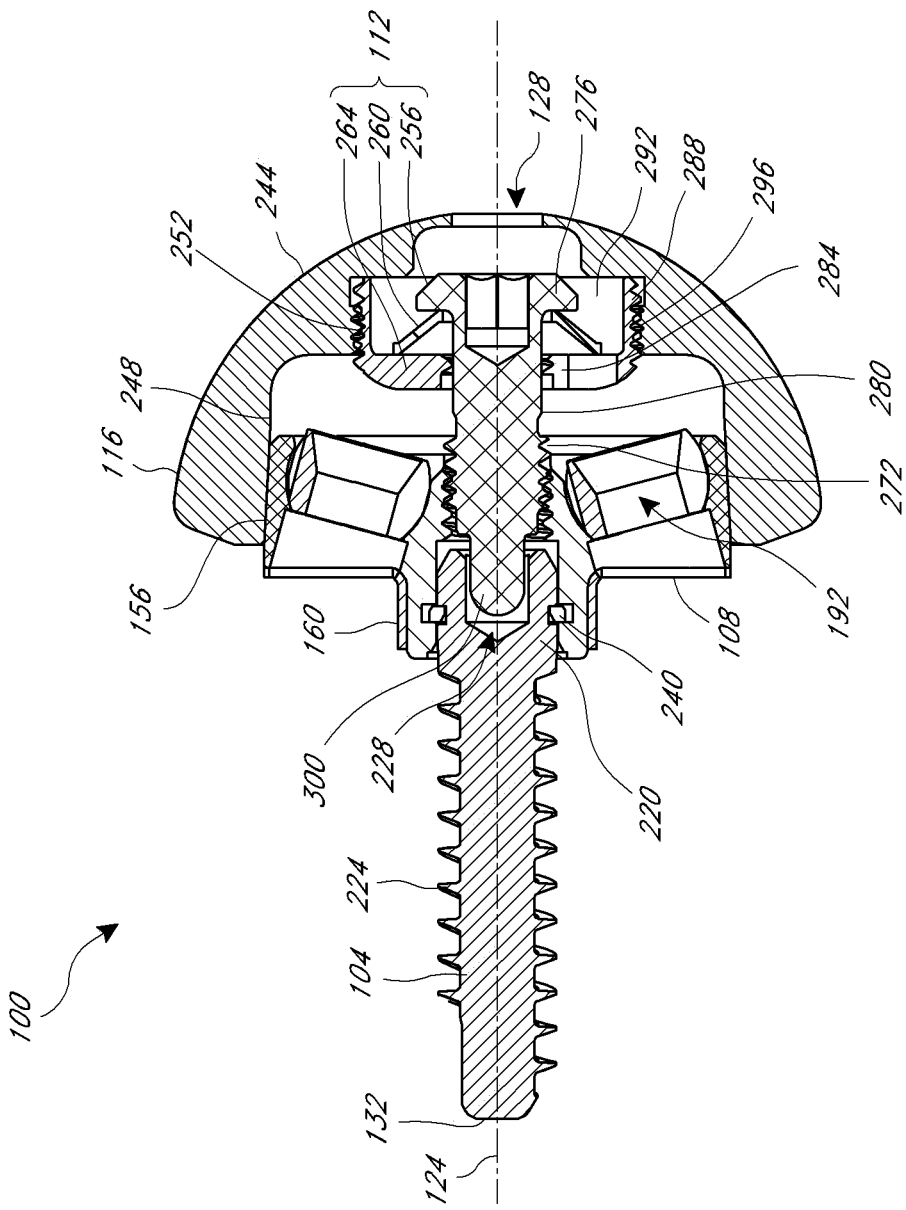
FIG. 4 is a cross-sectional side view of the glenoid implant shown in FIG. 2.

FIGS. 2-4 depict a glenoid implant 100, more preferably a reverse glenoid implant, configured to be implanted in the glenoid cavity of a patient in the patient's scapula. The glenoid implant 100 includes an anchor member 104 for anchoring the implant 100 in the scapular glenoid, a baseplate 108, a locking structure 112 configured to deter rotation of the anchor member relative to the baseplate, and a glenosphere 116 having an articular surface (e.g., a convex, spherical surface). The glenosphere 116 is configured to couple to a complimentary prosthetic device anchored to the humerus (not shown, but sometimes referred to herein as the humeral component) in order for the joint replacement implants to replicate the motion of the human shoulder. The humeral component can take any suitable form such as those disclosed in connection with FIGS. 18-21 and elsewhere in U.S. provisional application No. 61/719,835, filed Oct. 29, 2012, which is incorporated by reference herein in its entirety. Suitable humeral components can be configured to couple with reverse shoulder joint components, including those described in connection with FIGS. 1-9, 27-38, and 39-41 of the '835 application. Suitable humeral components can be configured to adapt to anatomical and reverse shoulder configurations. The glenoid implant 100 and the humeral component provide a replacement for the natural glenohumeral joint.

As used herein, the terms "distal" and "proximal" are used to refer to the orientation of the glenoid implant as shown in FIGS. 2-4. As shown in FIG. 3, a longitudinal axis 120 of the glenoid implant 100 extends through a central longitudinal axis 124 of anchor member 104 (shown in FIGS. 4 and 6). The glenosphere 116 is towards the proximal end along the longitudinal axis 120 and the anchor member 104 is towards the distal end along the longitudinal axis 120. In other words, an element is proximal to another element if it is closer to a central aperture 128 (shown in FIG. 4) of the glenosphere 116 than the other element, and an element is distal to another element if it closer to a distal tip 132 (shown in FIG. 4) of the anchor member 104 than the other element. At some points below, reference may be made to the anatomical location. In use when the implant is delivered into a patient's scapula, the distal tip 132 of the anchor member 104 is more medial on the patient, whereas the articular surface of the glenosphere 116 is more lateral on the patient.

Figure 5:
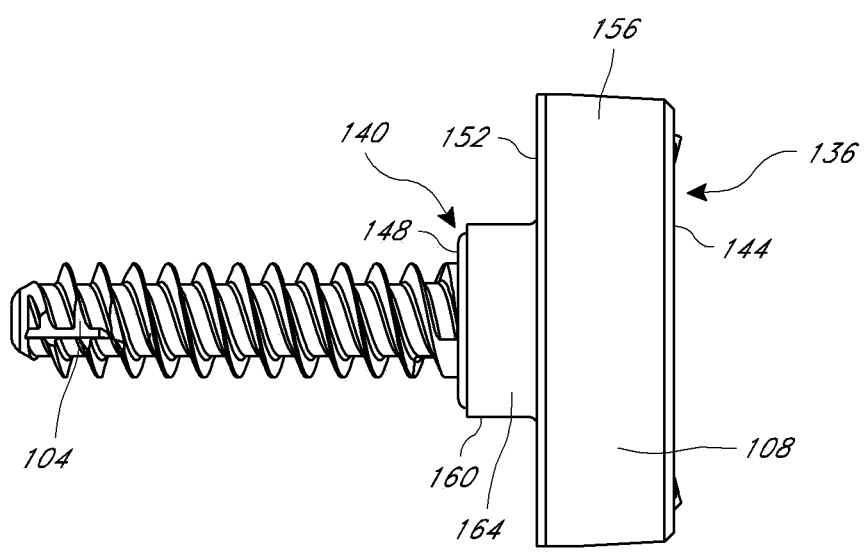
FIG. 5 is a side view of a baseplate and an anchor member of a glenoid implant.
Figure 8A:
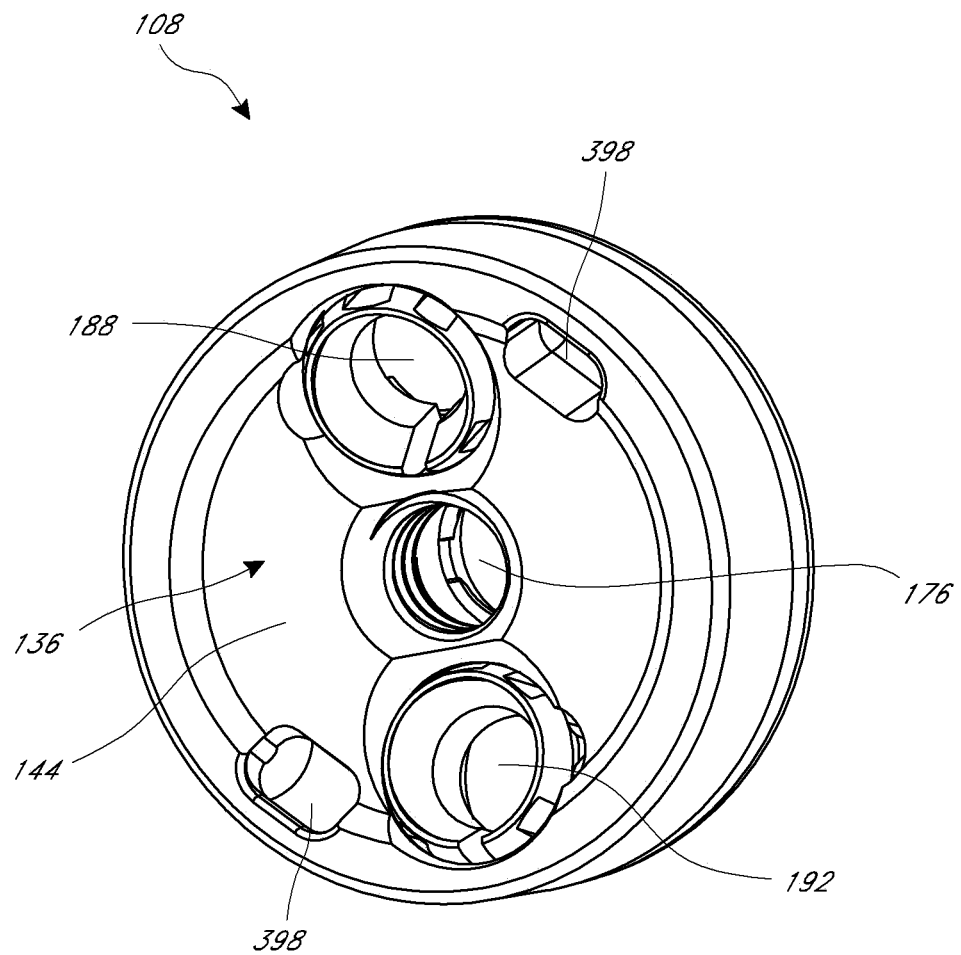
FIG. 8A is a top perspective view of a baseplate.

FIGS. 3 and 4 show that the baseplate 108 is oriented substantially perpendicular to the longitudinal axis 120 of the glenoid implant 100. The baseplate 108 is shown coupled to the anchor member 104 in FIGS. 4 and 5 and apart from the anchor member 104 in FIG. 6. Referring now to FIG. 5, the baseplate 108 has a proximal end 136 and a distal end 140. The proximal end 136 comprises a proximal surface 144 and the distal end 140 comprises a distal surface 148. The proximal surface 144 can be substantially parallel to the distal surface 148. The baseplate 108 can also include a bone engaging surface 152. A thickness of the baseplate 108 defined between the proximal surface 144 and the bone engaging surface 152 may correspond to the amount that the baseplate 108 extends above a surface of the bone when implanted. The thickness can be in a range between about 2 mm and about 12 mm, e.g., between about 4 mm and about 9 mm, e.g., about 6 mm. Thicknesses of about 3 mm, 5 mm, 7 mm, 8 mm, 10 mm and 11 mm are also contemplated. As discussed further below, FIG. 8J illustrates a modified embodiment of a baseplate 108J where the surface 144 is lateralized relative to the patient's mid-plane. A lateralized baseplate is one in which when combined with an articular component, the articulating surface is shifted laterally relative to the medical plane of the patient compared to an anatomical position of the articular surface. In the context of a reverse shoulder, the shifting can move the center of rotation of the humerus laterally compared to the position of the center of rotation prior to intervention. In the context of an anatomic shoulder prosthesis, the lateralized baseplate may support an anatomic articular surface that is shifted laterally relative to the medial surface compared to the glenoid surface prior to intervention. The bone engaging surface 152 can be substantially parallel to the proximal surface 144 and/or the distal surface 148. FIGS. 8K-8L illustrate modified embodiments in which the bone engaging surface varies, e.g., providing a partial or full wedge shape for reasons discussed below.

The baseplate 108 also has a lateral surface 156 that spans between the proximal surface 144 of the baseplate 108 and the bone engaging surface 152 of the baseplate 108. The surface 156 is disposed lateral with regard to the center of the implant 100 and also is disposed lateral of the mid-plane of the patient when the implant 100 is applied to the patient. The lateral surface 156 can have a circular profile when viewed in a cross-section plane extending parallel to the proximal surface 144. The diameter of the circular profile can be between about 20 mm and about 40 mm, e.g., between about 25 mm and about 35 mm, e.g. about 30 mm. In some embodiments, the lateral surface 156 of the baseplate 108 is configured to form a portion of a friction lock engagement, such as a Morse taper. In one embodiment, the lateral surface 156 of the baseplate 108 is tronconical. The term tronconical, as used herein, refers to a shape or surface that is or is similar to a truncated cone. In some embodiments, the lateral surface 156 is configured with a gradually increasing perimeter in a direction from proximal surface 144 toward the bone engaging surface 152.

Figure 6:
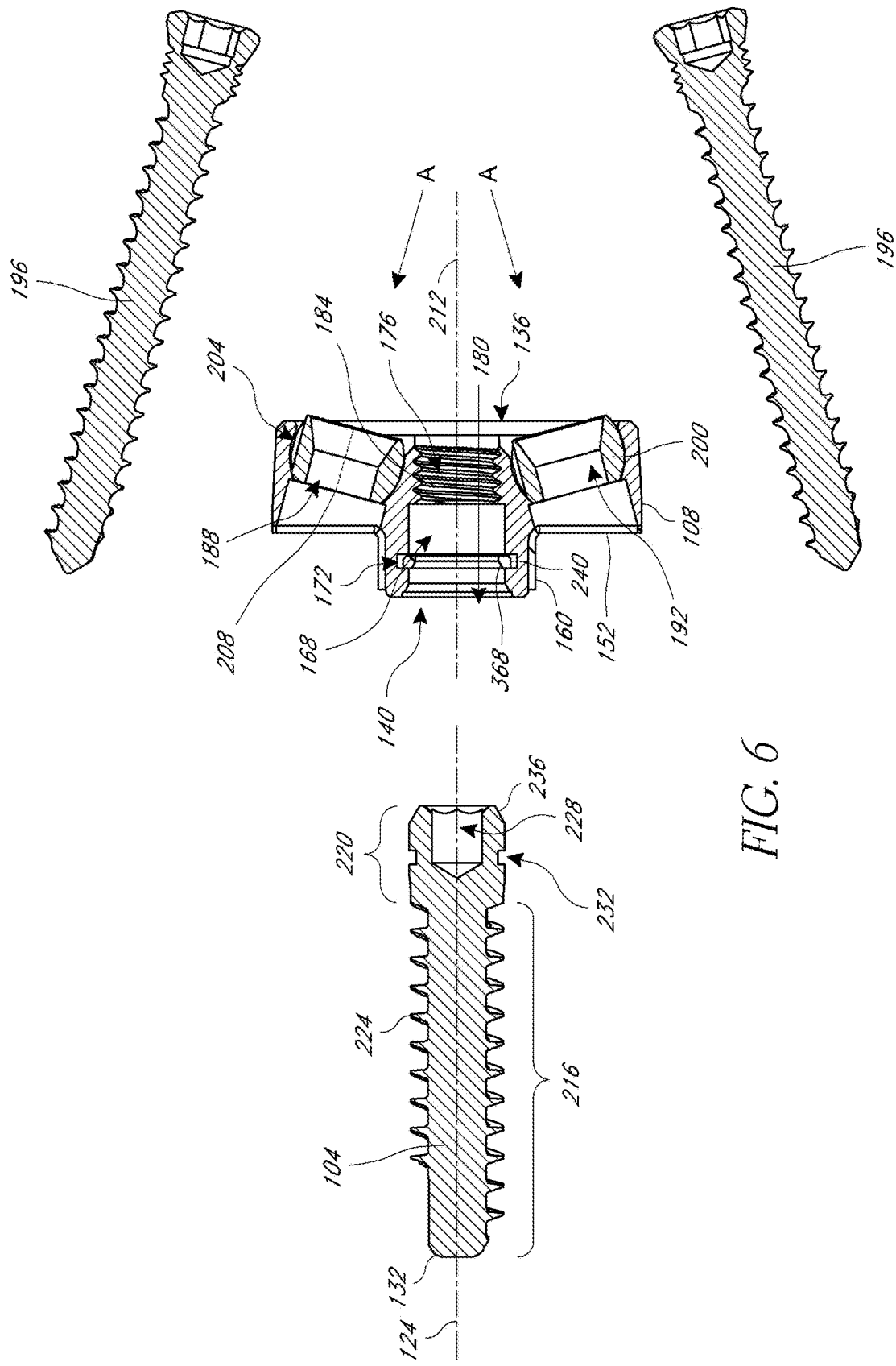
FIG. 6 is a cross-sectional, exploded side view of a baseplate, an anchor member and perimeter anchor members.

As illustrated in FIG. 5, in some embodiments, the baseplate 108 can include a central protrusion 160 that projects distally from the bone engaging surface 152 to the distal end 140. The central protrusion 160 has an outer surface 164 that extends from the bone engaging surface 152 to the distal surface 148. Referring now to FIG. 6, the central protrusion 160 can include a first aperture 168 which may be cylindrical. In some embodiments, the first aperture 168 may include a groove 172 along an inner wall of the first aperture. The baseplate 108 can have a second aperture 176 that, in some embodiments, extends from the first aperture 168 to the proximal end 136 of the baseplate 108, such that a lumen 180 is formed through the baseplate 108. The second aperture 176 can include an internally threaded surface 184 as shown. In some embodiments, the second aperture 176 is smaller in diameter than the first aperture 168.

FIG. 6 shows that the baseplate 108 includes a plurality of holes, e.g., two holes 188, 192 positioned laterally outward of the lumen 180, that are configured to accept perimeter anchor members 196. The holes 188, 192 extend from the proximal end 136 of the baseplate 108 to the bone engaging surface 152 of the baseplate 108. These holes 188, 192 are also illustrated in FIG. 8A, which illustrates a perspective view of the proximal end 136 of the baseplate 108 of FIGS. 2-6. As illustrated, the baseplate 108 may have a circular shape, with a thickness between the proximal surface 144 and the bone engaging surface 152 that is less than a diameter of the proximal surface 136. It will be appreciated that the baseplate 108 need not be circular, and may have other shapes as well.

Referring to FIGS. 3 and 6, the holes 188, 192 can be defined in part by internal members 200 that are disposed within recesses 204 in baseplate 108. In some embodiments, the internal member 200 is semi-spherical and the recess 204 is semi-spherical, in order to permit movement of, e.g., rotation and/or tilting of the internal member 200 with respect to the baseplate 108. The internal member 200 allows a longitudinal axis extending centrally through the holes 188, 192 (for example longitudinal axis 208 extending through hole 188 as shown in FIG. 6) to be aimed to some extent toward a desired anatomical feature. The movement of the internal member 200 allows the positioning and/or aiming of perimeter anchor members 196 toward a desired location. The longitudinal axis 208 extending through the hole 188 can be substantially parallel to a longitudinal axis 212 extending through the second aperture 176 and/or lumen 180, as shown by the orientation of the internal member 200 in part defining the hole 188 or angled with respect to the longitudinal axis 212 of the second aperture 176 and/or lumen 180, not shown.

The number and position of the holes 188, 192 depends on many factors including the anatomical structure of the patient, the diameter of the perimeter anchor members 196, and size constraints dictated by dimensions of the baseplate 108. Thus, there may be fewer or greater holes and perimeter anchors members than illustrated. In some embodiments, perimeter anchor members 196 are inserted through the baseplate 108 from the proximal end 136 thereof. As shown in FIG. 6, the perimeter anchor member 196 can be inserted in the general direction of Arrow A.

FIG. 6 shows that the anchor member 104 is configured to be attached to the bone of a patient. The anchor member 104 is generally formed of a cylindrical longitudinal portion 216 and a proximal head 220, both of which extend along a longitudinal axis 124 of the anchor member 104. The anchor member 104 has an external lateral surface 224 which may include a self-tapping threaded surface. Other lateral surfaces of anchor members are discussed below in connection with FIGS. 7A-7E, 8E, 9A, 9C and 9E. As used herein, a threaded surface is right-handed when the driving action is performed with clockwise rotation and left-handed when the driving action is performed with counterclockwise rotation. The threading of the external lateral surface 224 of the anchor member 104 may be right-handed or left-handed. In some embodiments, the longitudinal portion 216 of the anchor member 104 comprises a distally tapered distal tip 132.

FIG. 6 shows that the proximal head 220 can have a cavity 228 disposed about the longitudinal axis 124. The cavity 228 extends distally from the proximal end of the proximal head 220. In some embodiments, the cavity 228 comprises one or more flat surfaces that are capable of mating with a driver configured to apply rotational force to drive the anchor member 104 into the bone. For example, the cavity 228 can have a hexagonal cross-section, centered on the longitudinal axis 124, configured to mate with a hexagonal cross-section driver. The proximal head 220 can comprise a groove 232. In some embodiments, the groove 232 is a circumferential groove around an external surface of the proximal head 220. The proximal head 220 may include an inclined surface 236, the function of which is discussed in greater detail below.

Referring to FIGS. 5 and 6, the anchor member 104 and the baseplate 108 are coupled in the first aperture 168, which is sized to accept the proximal head 220 of the anchor member 104. In some embodiments, the glenoid implant 100 comprises a member 240, as shown in FIGS. 3, 4 and 6, that is sized to fit partly within the groove 232 in the proximal head 220 and partly within the groove 172 in the baseplate 108. The member 240 can comprise a c-clip, O-ring or similar protruding device that can span at least a portion of the groove 232 in the proximal head 220 and at least a portion of the groove 172 in the baseplate 108. Alternatively member 240 may be comprised of elastically deformable barbs, fingers, or other projections having one end attached to and angled away from either head 220 or baseplate 108 such that the projections are deformed between head and baseplate when head is inserted into baseplate and such that the unattached end of the projections elastically expands into groove in head or baseplate. In this way, the anchor member 104 is held at a fixed position along the longitudinal axis 120 of the glenoid implant 100, shown in FIG. 4, relative to the baseplate 108. Preferably the coupling provided by the member 240 does not prevent the relative rotation of the anchor member 104 and the baseplate 108. In some embodiments, as shown in FIGS. 4 and 6, the member 240 is retained within the groove 172 of the baseplate 108 before the proximal head 220 of the anchor member 104 is inserted into the first aperture 168.

FIG. 6 depicts the anchor member 104 separate from the baseplate 108, e.g., before being coupled to the baseplate. The anchor member 104 can be inserted from the distal end 140 of the baseplate 108 into the first aperture 168. During insertion, the inclined surface 236 of the proximal head 220 initially contacts the member 240. Further insertion of the anchor member 104 displaces the member 240 away from the axis 124, farther into the groove 172. Such displacement allows the anchor member 104 to be inserted farther into the first aperture 168. The anchor member 104 is inserted into the first aperture 168 until the member 240 engages the groove 232 in the proximal head 220. The anchor member 104 is retained in the baseplate 108 by the spanning of the member 240 across the gap between the longitudinally adjacent grooves 232, 172, as shown in FIG. 4.

In some embodiments, the member 240 is deformed by the proximal head 220 when the proximal head 220 is inserted into the first aperture 168. For example, the inclined surface 236 can provide a progressively larger force on the member 240 as the proximal head 220 is urged from the distal end 140 of the baseplate 108 proximally into the first aperture 168 of the central protrusion 160. The inclined surface 236 can have an angle of about 45 degrees or greater. In this context, the angle is measured relative to the flattened proximal end of the proximal head 220. In one embodiment, the member 240 has a corresponding inclined surface 368 (see FIG. 6) that faces distally. When the groove 232 in the proximal head 220 aligns with the groove 172 in the baseplate 108, the member 240 returns to a relaxed state, e.g., is no longer deformed and the member 240 functions to couple the anchor member 104 to the baseplate 108. More specifically, the member 240 couples the proximal head 220 to the first aperture 168.

Figure 6A:
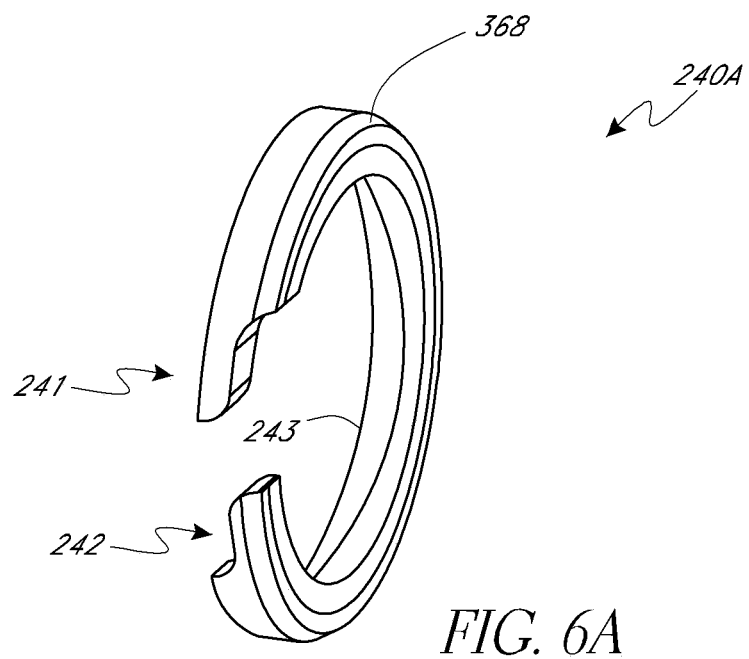
FIG. 6A illustrates an embodiment of an anchor retention member.

FIG. 6A illustrates a member 240A having mating ends. In particular, the clip member 240A has a first end 241, a second end 242, and an arcuate segment 243 therebetween. The inclined surface 368 is provided along a distal-facing side of the arcuate segment 243. The first and second ends 241, 242 are configured to mate or nest together when urged toward each other. For example, the first end 241 can have a reduced thickness on the distal facing side thereof and the second end 242 can have a reduced thickness on a proximal facing side thereof. The reductions in thickness of the first and second ends 241, 242 can sum to the total thickness of the arcuate segment 243 or more in various embodiment. As a result, the ends 241, 242 can move from a spaced apart configuration to an overlapping configuration with minimal to no deflection of the ends 241, 242 in a proximal-distal direction being required. Alternatively, the reductions in thickness of the first and second ends 241, 242 can sum to less than total thickness of the arcuate segment 243. In such embodiments, upon causing the ends 241, 242 to overlap, deflection of the ends along the proximal-distal direction will occur causing a widening of the clip 240A in the region of the ends 241, 242 compared to in the arcuate segment 243. FIG. 6A illustrates an enlarged configuration of the member 240A, e.g., a configuration in which an anchor member is being inserted and the clip member 240A is enlarged to permit advancement of a head of the anchor member through the clip member 240A and a corresponding baseplate. These structures are examples of various means for preventing axial translation of the baseplate 108 relative to the anchor member 104 while permitting rotation therebetween.

FIG. 4 shows that the glenosphere 116 defines a convex, articular surface 244. The glenosphere 116 defines an interior surface 248 configured to receive the baseplate 108. In particular, the interior surface 248 of the glenosphere 116 is configured to couple with the lateral surface 156 of the baseplate 108. In some embodiments, the interior surface 248 of the glenosphere 116 is configured to frictionally engage the surface 156, e.g., in a Morse taper. In some embodiments, the interior surface 248 of the glenosphere 116 is tronconical. The glenosphere 116 can include an internal threaded surface 252. In some embodiments, the glenosphere 116 comprises a creep-resistant material, such as a suitable metal including any of stainless steel, cobalt-chrome alloy, or titanium which permits the interior surface 248 to deflect slightly in connection with forming a secure connection such as a Morse taper.

Referring to FIGS. 3 and 4, the locking structure 112 can include a locking screw 256, a compression washer 260, and a threaded member 264, which may be a bushing. The locking screw 256 has a body that extends along the longitudinal axis 120 when the assembly 100 is assembled. The locking screw 256 can have an external threaded surface 272 and a proximal head 276, as shown in FIG. 4. A lateral surface 280 of the locking screw 256 located between the external threaded surface 272 and the proximal head 276 has a smooth surface, e.g., one that is not threaded. In some embodiments, a driver can be introduced into the proximal head 276 of the locking screw 256 in order to rotate the locking screw 256. The compression washer 260 is generally annular in shape in one embodiment. The threaded member 264 includes one or more internal threads 284 configured to mate with the external threaded surface 272 of the locking screw 256. The threaded member 264 can include a sidewall 288 that forms an internal cavity 292 configured to house the compression washer 260. The sidewall 288 can have an external threaded surface 296 that is configured to mate with an internal threaded surface 252 of the glenosphere 116. The glenoid implant 100 is configured to be assembled as shown in FIGS. 2 and 4.

FIG. 4 shows that during assembly of the locking structure 112, the compression washer 260 can be inserted into the internal cavity 292 of the threaded member 264 and housed within the sidewall 288. The locking screw 256 can be inserted through the compression washer 260 from the proximal end to the distal end thereof. A portion of the external threaded surface 272 of the locking screw 256 passes through the central aperture of the compression washer 260. The locking screw 256 can be inserted into the threaded member 264 such that the external threaded surface 272 of the locking screw 256 mates with the internal thread(s) 284 of the threaded member 264. The locking screw 256 can be further rotated until the compression washer 260 is loosely retained between the threaded member 264 and the proximal head 276 of the locking screw 256. The smooth lateral surface 280 can be disposed within the internal threads 284 of the threaded member 264, when the compression washer 260 is loosely retained.

The locking structure 112, which can include the locking screw 256, the compression washer 260, and the threaded member 264, can be coupled to the glenosphere 116, as shown in FIG. 4. In some embodiments, the locking structure 112 is coupled to the glenosphere 116 after the locking structure 112 has been assembled, as described above. The threads on external surface 296 of the sidewall 288 of the threaded member 264 can be rotated to engage the internal threaded surface 252 of the glenosphere 116. This may involve rotation of the locking screw 256 toward the threaded member 264, so that the proximal head 276 of the locking screw 256 fits within the glenosphere 116. The glenosphere 116 can have a central aperture 128 that allows access to the proximal head 276 of the locking screw 256. The central aperture 128 permits a driver or other tool to engage the locking screw 256. As shown in FIG. 4, the proximal head 276 of the locking screw 256 can have a cavity with one or more flats, e.g., a hexagonal cavity, configured to mate with the driver.

The locking structure 112 can be coupled to the baseplate 108, as shown in FIG. 4. In some embodiments, the locking structure 112 is coupled to the baseplate 108 after the locking structure 112 has been assembled, as described above. In some embodiments, the locking structure 112 is coupled to the baseplate 108 after the locking structure 112 is coupled to the glenosphere 116, as described above. The locking screw 256 can be rotated until the external threaded surface 272 of the locking screw 256 engages the second aperture 176 in baseplate 108, in particular the threaded surface 184 (See FIG. 6). When the locking screw 256 is rotated, the locking screw 256 traverses the second aperture 176 distally toward the anchor member 104. Further rotation of the locking screw 256 brings the distal tip 300 of the locking screw 256 into contact with the proximal head 220 of the anchor member 104. In some embodiments, the distal tip 300 of the locking screw 256 enters the cavity 228. The locking screw 256 is capable of applying a force to the proximal head 220 of the anchor member 104. In some embodiments, this downward (e.g., distally directed) force applies a compression force to the member 240 such that the member 240 applies a frictional force to the groove 232 on the proximal head 220. A friction force will also be applied by the distal tip 300 to the wall at the distal end of the cavity 228. The distally directed forces created by the locking screw 256 on the anchor member 104 and/or the member 240 are sufficient to reduce or prohibit the rotation of the anchor member 104 with respect to the baseplate 108. For example, high friction can arise due to the high normal force generated by action of the locking screw 256.

Referring to FIG. 4, when the locking screw 256 is rotated and advanced towards the anchor member 104, the locking screw 256 can cause a force to be applied to the glenosphere 116. Rotation of the locking screw 256 can move the proximal head 276 toward the distal end of the threaded member 264. Rotation of the locking screw 256 can bring the proximal head 276 of the locking screw 256 into contact with the compression washer 260. In some embodiments, the proximal head 276 of the locking screw 256 can apply a downward force on the compression washer 260. The compression washer 260 can thereby apply a downward force on the threaded member 264. The threaded member 264 including the sidewall 288 can be coupled with the internal threaded surface 252 of the glenosphere 116. The threaded member 264 can provide a downward force on the glenosphere 116, as the locking screw 256 is advanced distally toward the anchor member 104. This causes the glenosphere 116 to move distally and engage the lateral surface 156 of the baseplate 108.

FIG. 4 shows that the lateral surface 156 of the baseplate 108 is tapered, e.g., tronconical, in some embodiments. The glenosphere 116 defines an interior surface 248 that is tapered or tronconical or otherwise configured to create high friction with the baseplate 108. The surfaces 156, 248 can be initially engaged in any suitable manner, e.g., using an impactor to create an initial frictional engagement therebetween. In some embodiments, the lateral surface 156 of the baseplate 108 and the interior surface 248 of the glenosphere 116 form a Morse taper. The distally directed force of the locking screw 256 enhances, e.g., makes more rigid, the connection between the anchor 104 and baseplate 108, reducing or eliminating play between these components. As a secondary advantageous effect, the distally directed force of the locking screw 256 can also increase the friction at the surfaces 156, 248. The frictional force created by the coupling of the glenosphere 116 and the baseplate 108 add to the rigidity of the glenoid implant 100.

The compression washer 260 shown in FIG. 4 can have multiple functions. The compression washer 260 is configured to fill the space between the proximal head 276 of the locking screw 256 and the threaded member 264 to add to the rigidity of the implant 100. In particular, rotation of the locking screw 256 applies a force on the compression washer 260 which can compress or otherwise deform the compression washer 260. In the compressed state, the compression washer 260 applies a force to maintain the position of the locking screw 256. The placement and use of the compression washer 260 facilitates the rigidity of the glenoid implant 100 by filling the space between the proximal head 276 of the locking screw 256 and the threaded member 264. Additionally, the locking screw 256 applies a force to the anchor member 104. This force enhances the connection of the anchor member 104 to the baseplate 104 which reduces or eliminate play between these components to minimize or reduce loosening of these components over time. For example, maintaining the position of the locking screw 256, the compression washer 260 further minimizes or prevents rotation, translation, or micromotion of the anchor member 104 with respect to the baseplate 108. In some embodiments, the compression washer 260 tends to distribute the force of the proximal head 276 of the locking screw 256. The compression washer 260 causes the proximal head 276 of the locking screw 256 to be in contact with a larger surface area of the threaded member 264. The distribution of force facilitates the downward movement of the glenosphere 116 with respect to the baseplate 108 and/or enhances friction between the surfaces 156, 248 as discussed above. The compression washer 260 further minimizes or prevents rotation, translation, or micromotion of the glenosphere 116 with respect to the baseplate 108.

The glenoid implant 100 can have a modular design, meaning that the anchor member 104 and the baseplate 108 can be interchangeable with another anchor member and/or another baseplate. In some embodiments a single baseplate can couple with any one of a plurality of anchor members in a kit including a plurality of anchor members, such as shown in FIGS. 7A-7E. In some embodiments, a single anchor member can couple with any one of a plurality of baseplates in some or in another kit, including for example the baseplates shown in FIGS. 8A-8G. The proximal heads of the anchor members can have a consistent diameter among a plurality of anchor members in some kits. Further, the grooves and the cavities of the anchor members can be consistent in size and location among a plurality of anchor members in some kits. In some embodiments, the grooves and first apertures of the baseplates is a consistent diameter among a plurality of baseplates in the kit. Further, the second apertures and the lumens of the baseplates can be consistent in size and location among a plurality of baseplates. This allows for the interchangeability of the plurality of anchor members with any one of a plurality of baseplates or the plurality of baseplates with any one of a plurality of anchor members.

FIGS. 7A-7E show that the modular design allows the use of a plurality of anchor members with a given baseplate. In FIGS. 7A-7E, the anchor members 104A-104E include a longitudinal portion 216A, 216B, 216C, 216D or 216E, a distal end, a proximal head 220, and a groove 232. The anchor members 104A-104E shown in FIGS. 7A-7E are compatible with the baseplates 108, described herein. The anchor members 104A-104E may include additional features of anchor members described herein.

Figure 7A:
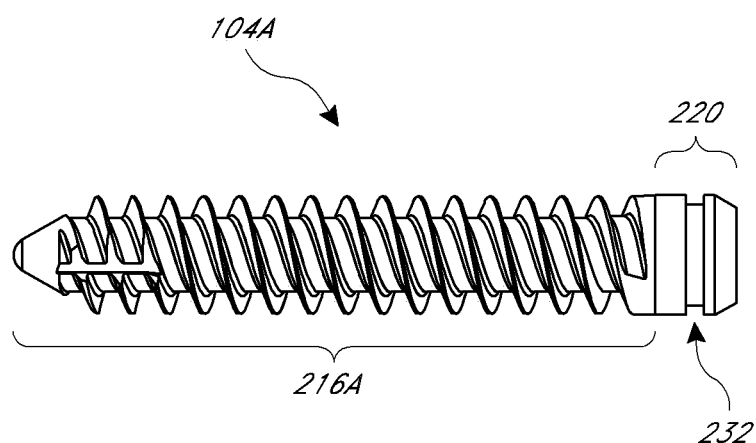
FIGS. 7A-7E are side views of different embodiments of anchor members, which may be assembled into a kit.
Figure 7B:
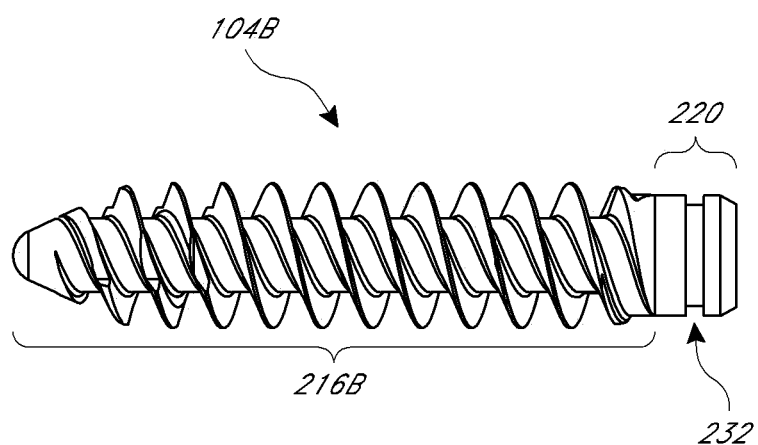
Figure 7C:
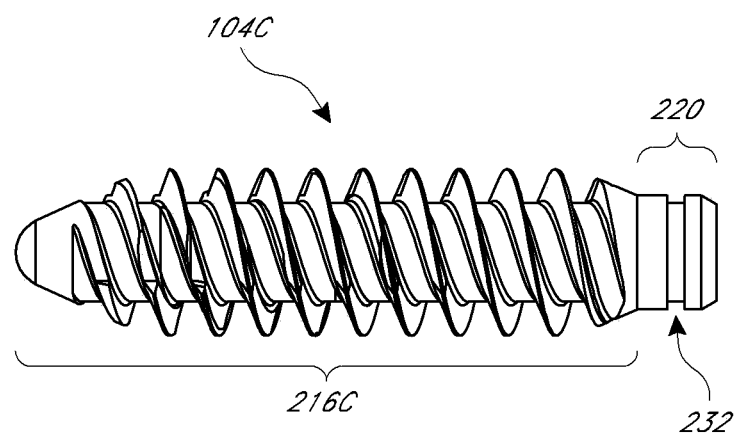

FIGS. 7A-7C differ with respect to the external lateral surface and the longitudinal portion of the anchor member. The anchor members 104A, 104B, 104C may have a longitudinal portion 216A, 216B, 216C having different configurations, e.g., diameters and/or lengths. The longitudinal portion 216A of anchor member 104A has a constant diameter and thread pitch, but different lengths in different embodiments. The anchor member 104B has a different diameter and/or thread pitch from the anchor member 104A. The anchor member 104C has a different diameter and/or thread pitch from the anchor members 104A and 104B.

As shown in FIGS. 7A-7C, the anchor members 104A-104C can have a different diameter in the longitudinal portions 216A-216C. In some embodiments, the diameters are in the range of 6.5 mm to 9.5 mm. Larger diameter anchor members can be useful for revision of total shoulder arthroplasty or failed reverse shoulder arthroplasty. The anchor members of the plurality of anchor members can have different lengths, and in some embodiments the lengths of the anchor member can be in the range of 15 mm to 40 mm. The external lateral surface is configured to engage a bony surface. The configurations shown in FIGS. 7A-7C demonstrate the ability to provide, e.g., in a kit, a plurality of anchor members from which a particular anchor member can be selected based on the anatomy of a patient.

Figure 7D:
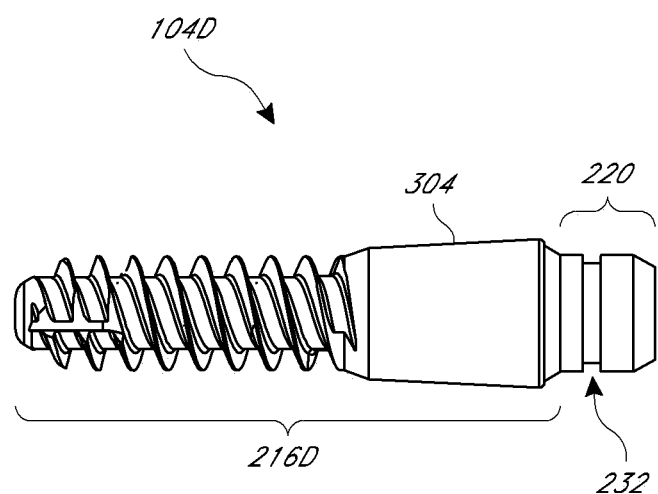

FIG. 7D depicts another embodiment of an anchor member 104D. The anchor member 104D has a cylindrical section of material along the longitudinal portion 216D of the anchor member 104D. The cylindrical section includes porous material 304 to promote bony ingrowth. That is, bone material can grow into the pores of the cylindrical section of porous material 304. The longitudinal portion 216D may include an external threaded surface to engage bone. FIGS. 7A-7D show the proximal head 220 of the anchor members 104A-104D may have a consistent configuration. For example, the proximal head can have a unitary diameter among a plurality of anchor members. The anchor member may include a groove that engages member 240 as described above.

Figure 7E:
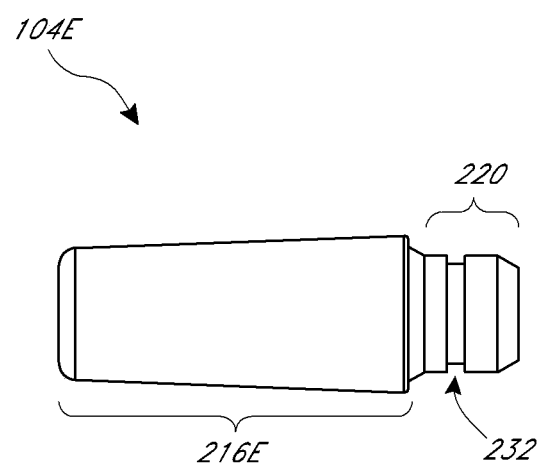

FIG. 7E shows an anchor member 104E. The longitudinal portion 216E can include an external lateral surface that is generally without threads to be tapped or otherwise pressed into the bone. The external lateral surface may be comprised of ridges, circumferential ridges, rough coatings, knurling, plasma sprayed metal, or other rough surfaces that will increase the friction of the longitudinal portion 216E relative to the bone thereby helping to prevent longitudinal portion 216E from pulling out of the bone. The anchor member 104E comprises a proximal head 220 that is the same as the proximal heads in the anchor members of FIGS. 7A-7D. The longitudinal portion 216E can be tapered, e.g., having a narrower transverse profile adjacent to its distal end and a wider transverse profile adjacent to the head 220. The proximal head 220 has a groove 232 that couples with the baseplate 108 in the same manner as the other anchor members discussed herein. The anchor member 104E provides additional options for the interchangeable anchor member.

The anchor members 104, 104A-104E (described above) and 312 (described below in connection with FIG. 9A) can be made from a biocompatible material such as a metal alloy, polymer, or ceramic. For example, anchor members can be made from stainless steel, titanium, titanium alloy, cobalt-chrome alloy, and/or PEEK. In some embodiments, the anchor member 104, 104A-104E, 312 is more rigid than the baseplate 108. The rigidity of the anchor member 104, 104A-104E, 312 prevents deformation of the anchor member during insertion into the bone and during use as a glenoid implant.

FIGS. 8A-8L illustrate embodiments of baseplates having features similar to those described above and/or additional features. One or more of these features may be interchanged or incorporated into any of the baseplates described herein. In the embodiment of FIGS. 8A, G and H, on the proximal surface 144, the baseplate 108, 108G, 108H is illustrated with tool engaging grooves or openings 398. The tool engaging grooves 398 are configured to engage two radially extending legs of a tool described below with reference to FIG. 10. The grooves 398 can be present on any of the embodiments of the baseplate described herein.

Figure 8C:
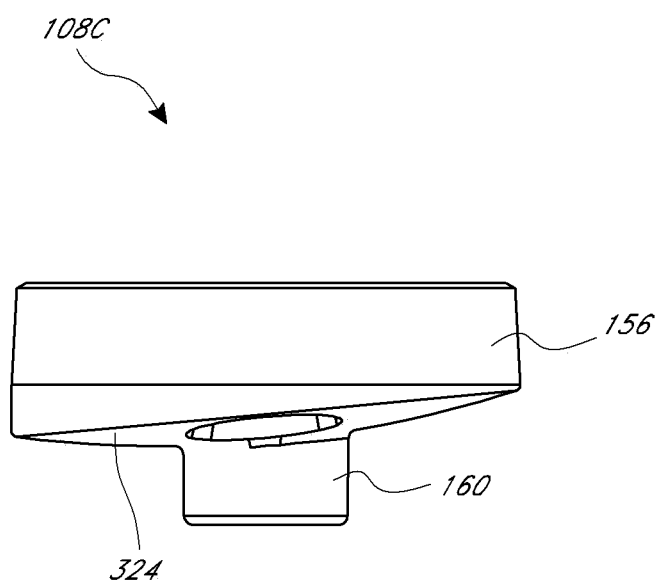

As shown in the embodiments of FIGS. 5, 8A-8C and 8F-8H, the central protrusion 160 is centrally disposed relative to the lateral surface 156 of the baseplate 108. For example, a central longitudinal axis of the central protrusion 160 can be disposed equidistant from points along the lateral surface 156, as shown in FIG. 5. FIGS. 8B-8L illustrate more features of baseplates that can be combined with and/or substituted for features illustrated in the embodiment of FIGS. 5 and 8A. For example, FIGS. 8B-8E illustrate baseplates 108B-108D with configurations that can augment or compensate for scapula bone loss. FIG. 8B shows that the baseplate 108B has a proximal surface 144B. FIG. 8B shows that the bone engaging surface 320 has a curved surface (e.g., a convex surface). The bone engaging surface 320 is symmetrical with respect to the central protrusion. FIG. 8C shows that the bone engaging surface 324 of the baseplate 108C has an anatomically curved surface. The curved surface can be nonsymmetrical with respect to the central protrusion. The curved surface can be selected by the surgeon to match an anatomic feature of the patient's bone. The bone engaging surfaces 152, 320, 324 can match the curvature of the glenoid cavity of the patient.

FIGS. 8J-K illustrate further baseplates 108J-108K that can compensate for bone loss, thereby augmenting the bone at the joint. The baseplate 108J has a proximal portion 136J and a distal portion 140J. The proximal portion 136J can incorporate any of the features or components of the proximal end 136 of the baseplate 108 of FIGS. 2-6, 8A, and 10 or of proximal ends of other baseplates herein. The distal portion 140J is formed by a process of additive manufacturing, which is discussed below. The additive manufacturing process creates a porous titanium structure on the distal surface of the baseplate. In particular, the distal surface 148J and central protrusion 160J comprise the porous titanium structure described herein. The distal surface 148J can be a surface that extends radially outward from the central protrusion 160J and engages an exposed face of the glenoid. The central protrusion 160J can be configured to be advanced into the bone distal of the bone surface contacted by the distal surface 148J. The porous titanium structure can be disposed throughout the distal portion 140J, which contact the scapula at the glenoid surface. Any technique can be used to form the entirely of the distal portions of the baseplates herein, including additive manufacturing. Additive manufacturing can be used to provide a porous titanium structure in the entirety of the distal portions of the baseplates, including the central protrusions. This approach can provide a monolithic portion, e.g., where the same porous structure extends through the entire thickness of the monolithic portion of the baseplate.

The baseplate 108J also includes an augment portion 150J. The augment portion 150J is configured to move a proximal surface 144J of the baseplate 108J to a selected location and/or to replace or in-fill areas of bone loss with or without a lateral shifting of the center of rotation of the humerus at the shoulder joint. For example, the baseplate 108J may be applied to the patient by attaching it to the glenoid region of the scapula. In certain patients, wear of the glenoid may be substantially uniform. Uniform wear causes the pre-implantation glenoid surface to be shifted medially compared to an un-worn and/or un-diseased position of the glenoid surface. In such patients, the augment portion 150J shifts the location of baseplate 108J and thereby the articulating surface of a glenosphere coupled with the baseplate 108I. The baseplate 108J shifts the position of the glenosphere laterally. The position of the surface 144J of the lateralized baseplate 108J would be more lateral compared to the position of the same surface of the baseplate 108I that would result if the baseplate 108I were used. That is surface 144J would be farther from the medial plane of the body than would be the surface 144I on the same patient with the same glenoid condition.

FIG. 8K shows a baseplate 108K that is similar to the baseplate 108J except as described differently below. The baseplate 108K has an augment portion 150K that is non-uniform in thickness. The augment portion 150K can be formed in any suitable way, for example by additive manufacturing producing a porous metal structure. The augment portion 150K presents a first thickness, t1, along one peripheral side of the baseplate 108K and a second thickness, t2, along a second peripheral side of the baseplate. The second thickness is larger than the first thickness. The second thickness can be provided by progressively thickening the augment portion 150K in a lateral direction (e.g., toward the left in FIG. 8K). In the illustrated embodiment, the thickness of the augment portion 150K linearly increases across the width of the baseplate 108K. In the illustrated embodiment, a distal surface 148K is provided that engages the surface of the scapula, e.g., at the glenoid. The surface 148K has a first peripheral portion 146K that is parallel to a proximal surface 144K of the baseplate 108K. The surface 148K has a second peripheral portion 149K that is disposed at an angle relative to the proximal surface 144K. The angle between the second peripheral portion 149K and the proximal surface 144K can be selected based on the amount of bone to be replaced or supplemented by the augment portion 150K. The first peripheral portion 146K of the surface 148K can be located closer to the proximal surface 144K than is the second peripheral portion 149K of the surface 148K. The augment portion 150K provides a partial wedge, e.g., a half-wedge configuration. The augment portion 150K is for augmenting bone degeneration and/or disease in the location beneath a glenoid implant including the baseplate 108K. Although the embodiment of FIG. 8J could be used where uneven wear or disease is provided, the baseplate 108K can be advantageously used in a bone preserving manner such that the un- or less worn portions which would be disposed beneath the first peripheral portion and the less-thick region of the second peripheral portion need not be reamed or otherwise removed to accommodate the baseplate 108K. In various embodiments, the entire distal portion of the baseplate 108K can be made of a porous structure, e.g., of a porous titanium structure, as discussed herein. The porous titanium structure can be formed by additive manufacturing. The augment portion 150K can be made of a porous structure, e.g., of titanium formed by additive manufacturing.

FIG. 8L shows a baseplate 108L that is similar to the baseplate 108K except as described differently below. In the baseplate 108L an augment portion 150L is provided that augments bone loss across the entire glenoid surface. In the half-wedge embodiment of FIG. 8K, the angled portion 149K starts or ends inward of the outer periphery of the baseplate 108K. For example, the angled portion 149K can start adjacent to or at the central protrusion 160K. In the full wedge configuration of the baseplate 108L of FIG. 8L, the angled portion 149L starts or ends at or adjacent to a peripheral portion of the baseplate 108L and starts or ends at the second peripheral portion, augment extends the full length of the implant The baseplate 108L has an augment portion 150L that is non-uniform in thickness. The augment portion 150L can be formed in any suitable way, for example by additive manufacturing producing a porous titanium structure. The augment portion 150L presents a first thickness, T1, along one peripheral side of the baseplate 108L and a second thickness, T2, along a second peripheral side of the baseplate. The second thickness T2 progressively, e.g., linearly, decreases compared to the first thickness T1 in one embodiment across the width of the baseplate 108L. In the illustrated embodiment, a distal surface 148L is provided that engages the surface of the scapula, e.g., at the glenoid. The surface 148L has a first peripheral portion 149L that is parallel to a proximal surface 144L of the baseplate 108L. The surface 148L has a second peripheral portion 145L that is disposed at an angle relative to the proximal surface 144L. The angle between the second portion and the proximal surface 144L can be selected based on the amount of bone to be replaced or supplemented by the augment portion 150L. The first peripheral portion of the surface 148L can be located farther from the proximal surface 144L than is the second peripheral portion of the surface 148L. The augment portion 150L provides a full-wedge configuration. The augment portion 150L is for augmenting bone degeneration or disease in the location beneath a glenoid implant including the baseplate 108L. Although the embodiment of FIG. 8L could be used where uneven wear or disease is provided, the baseplate 108L can be advantageously used in a bone preserving manner such that the un- or less worn portions which would be disposed beneath the less-thick region of the second peripheral portion need not be reamed or otherwise removed to accommodate the baseplate 108L.

Among the advantages provided by using additive manufacturing to form an augment portion, such as the augment portion 150J, the augment portion 150K or the augment portion 150L is that the augment portion can be made patient specific in a fast and cost effective manner. For an individual patient, the need to replace or in-fill bone loss can be determined, such as by pre-operative imaging. The augment portion can be formed in accordance with this determination. In other words, the augment portion can be made to replace the lost bone, as determined pre-operatively, when fully integrated into the joint space, e.g., into the scapula or glenoid. This way the fit of the joint can be more accurate for an individual patient, which can lead to better outcomes such as by reducing the chance of post-operative patient discomfort and joint dislocation.

Figure 8D:
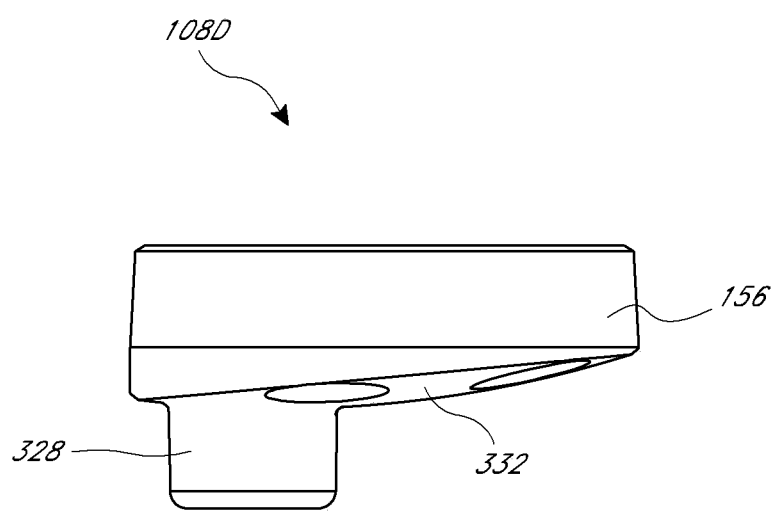
Figure 8E:
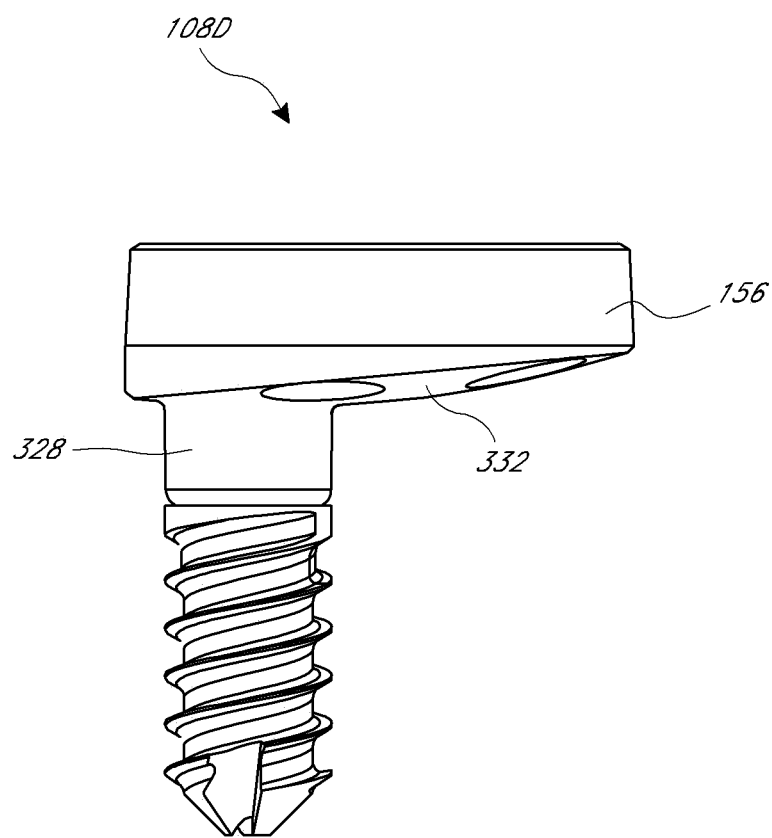

FIGS. 8D-8E illustrate that the protrusion 328 can be eccentric with respect to the baseplate 108D. In each of these embodiments, the protrusion 328 is not centrally disposed relative to the lateral surface 156 of the baseplate 108D. An anchor member such as anchor member 104 can be inserted into the protrusion 328, as discussed above with reference to central protrusion 160. When an anchor member is coupled to the baseplate 108D, the anchor member is eccentric with respect to the baseplate 108D.

Figure 8F:
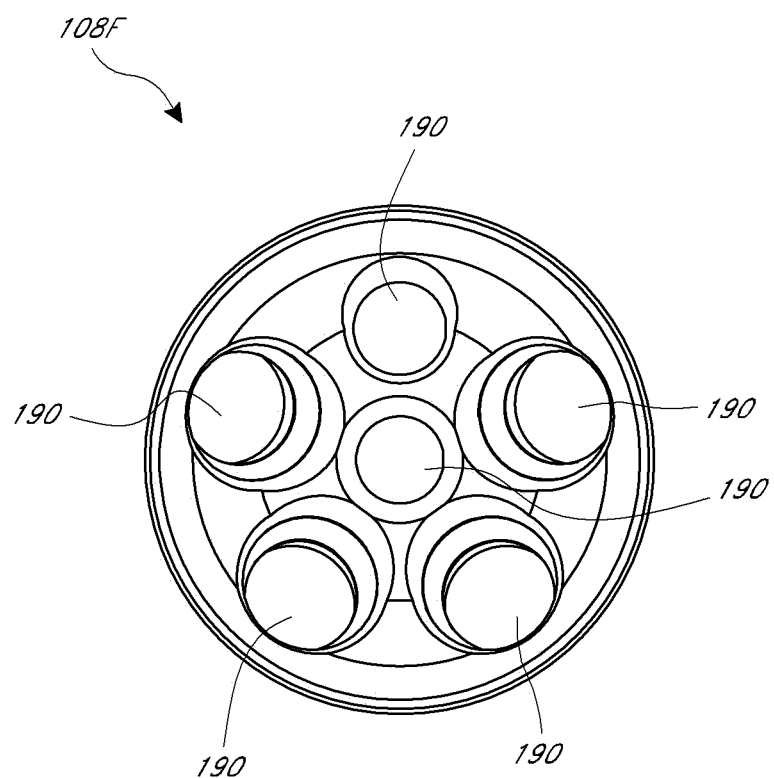
FIGS. 8F-8G are top views of different embodiments of baseplates.
Figure 8G:
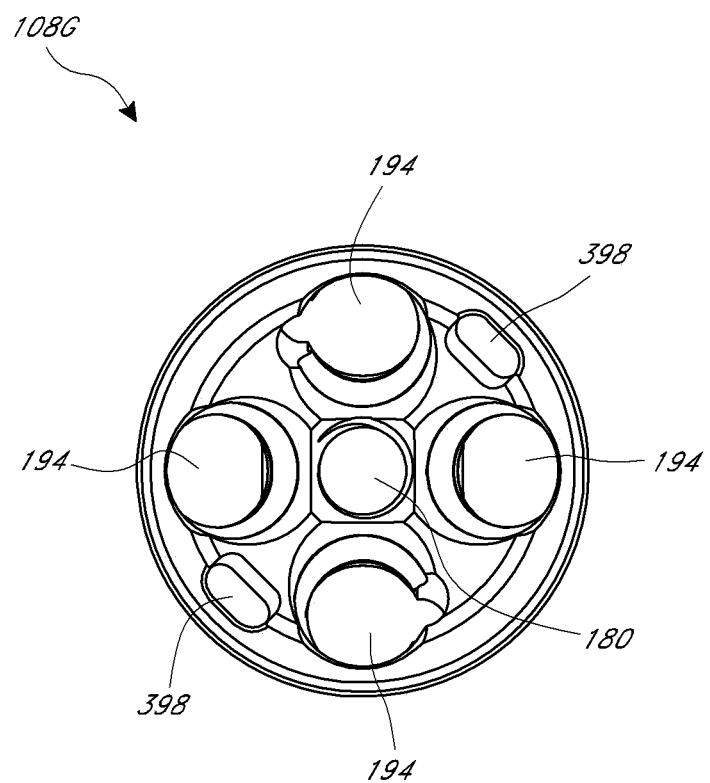
Figure 8H:
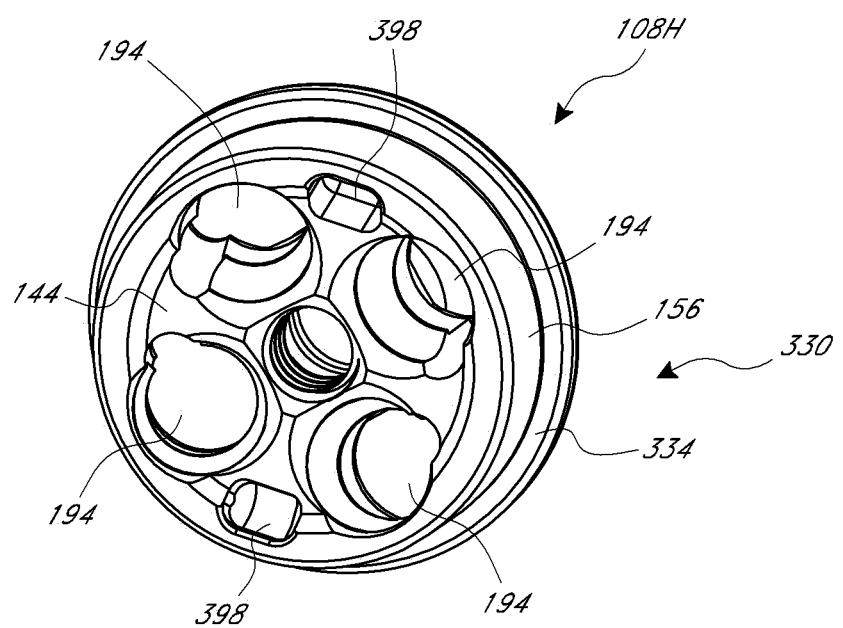
FIG. 8H is a top perspective view of another embodiment of a baseplate.
Figure 8K:
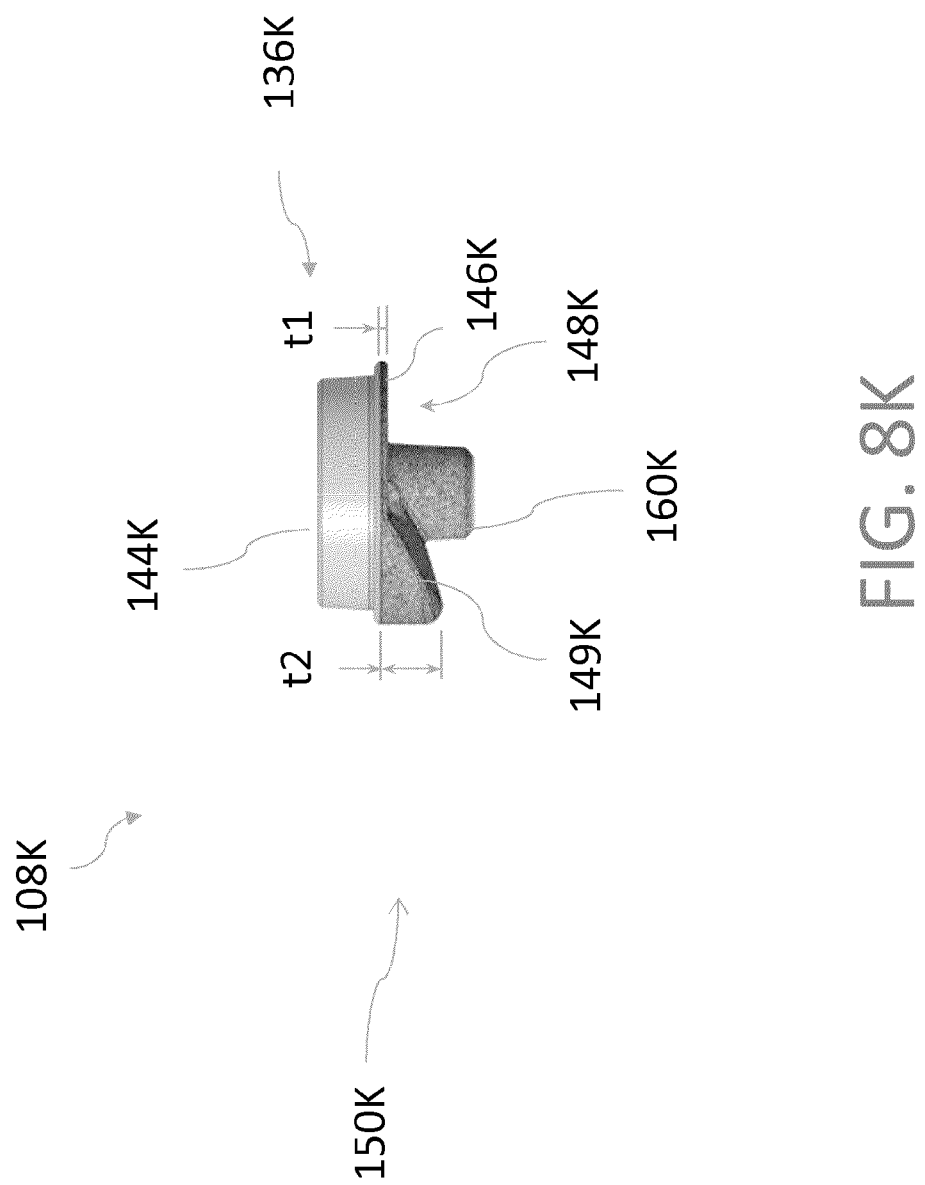
FIG. 8K is a half-wedge baseplate formed by additive manufacturing.

FIGS. 8F-8H each illustrate embodiments of a baseplate 108F, 108G, 108H with a plurality of holes, e.g., five, holes 190 or four holes 194. The holes are located around the periphery of the lumen 180. In some embodiments, the holes are equidistant with respect to each other, in other words, the holes are equally spaced around the lumen 180. FIG. 8G further illustrates that tool engaging grooves 398 may also be provided between holes 194.

FIG. 8H illustrates a baseplate 108H that has further features that can be combined with any of the other baseplates herein. The baseplate 108H has a radial protrusion 330 disposed between the proximal surface 144 and the bone engaging surface (not shown but opposite the surface 144). The radial protrusion 330 has a proximally oriented face 334. The face 334 can include an annular surface extending outward from a distal portion of the peripheral surface 156. In one embodiment, the face 334 abuts the glenosphere 116 when the glenoid implant 100 is fully assembled. The radial protrusion 330 can also define a positive stop for the distal advancement of the glenosphere 116 during assembly of the glenoid implant 100 such that the glenosphere is not overstressed by being advanced too far over the surface 156.

In embodiments, such as those illustrated in FIGS. 8I-8L, the baseplates are at least partially formed by additive manufacturing. In certain additive manufacturing techniques a material is applied to create a three dimensional porous metal structure. FIG. 8I shows a baseplate 108I that has a proximal end 136I and a distal end 140I. The proximal end 136I can incorporate any of the features or components of the proximal end 136 of the baseplate 108 or of proximal ends of other baseplates herein. The distal end 140I is formed by a process of additive manufacturing. More specifically, the portion of the baseplate that interacts with the bone may comprise a porous metal such as porous titanium (Ti-6Al-4V). As a result, the distal portions (e.g., the protrusion 146I and corresponding protrusions in other embodiments and/or the augment portion 150J-L) comprise a monolithic porous titanium structure, which contacts the scapula at the glenoid surface. Porous titanium has a modulus similar to bone or of about 2.6 GPa. Matching the modulus of the porous titanium to the bone may enable better stress transfer from the implant to the bone, reducing wear on the bone, and increasing strength at the bone/implant interface.

The porous titanium structure includes a pore size of from about 300 to about 800 μm, in embodiments from about 350 to about 750 μm in further embodiments from about 400 to about 700 μm. The porosity of the porous titanium structure may be optimized per implant geometry and anatomy and can be of about 50%, 55%, 60%, 65%, 70%, 75%, and 80%.

Porous titanium can be formed by an additive manufacturing process, including a 3 dimensionally (3-D) printing process where layers of titanium are formed to create a three dimensional structure. The initial layer or layers are formed by such a method directly onto a portion or surface of the baseplate. The 3-D printing process includes direct metal laser sintering onto the implant, more specifically, the baseplate. First, blanks are formed by sintering titanium powder with a laser directly onto the substrate or baseplate. Next, the blanks can be machined, constructed or shaped to create a specific geometry of the bone-engaging surface. In another technique, a machined blank is initially provided. Then, a first layer of a powder form of the material desired to make up the formed portion is disposed on and fused to the surface of the blank. After this, a second layer of the powder is applied to the part and is fused to the first layer and/or to the blank. This process is repeated to progressively build up the part. Any of the layers can be full or partial layers to impart complex geometries. After a plurality of layers is fused to the blank and to the other layers to form the desired geometry, including an irregular geometry if called for, the part can be further processed to eliminate any unfused powder. This process can produce a porous implant well adapted for being integrated into bone by bony ingrowth. In embodiments, the blanks are shaped to create either a lateralized (as in FIG. 8J), half-wedge (as in FIG. 8K) or full-wedge (as in FIG. 8L) augmented baseplate. Although the 3-D process is used herein to create augmented baseplates, other portions and surfaces of the implants may comprise porous titanium, and are within the scope of this disclosure, including, but not limited to central anchors or screws or portions thereof, peripheral anchors or screws or portions thereof and central posts. Once constructed, the porous structure and the solid substrate of baseplate comprise a monolithic, or one-piece, structure. Alternatively, Electron Beam Melting (EBM) can be used to 3-D print a porous structure on the implant.

FIGS. 9A and 9B illustrate an alternative embodiment of an anchor member 312 and a baseplate 336. The proximal head 340 of the anchor member 312 can include a threaded surface 344, as shown in FIG. 9A. The threads disposed on the surface 344 of the proximal head 340 of the anchor member 312 may be left-handed. The first aperture 348 in the baseplate 336 can include a threaded surface 352 configured to mate with the threads on the surface 344 of the proximal head 340. The threaded surface 352 of the first aperture 348 can be left-handed. Further, the baseplate 336 can comprise a central portion 356 that is not threaded. The central portion 356 can be surrounded by a smooth surface. The threaded surface in the aperture 348 is disposed between the smooth surface and a distal surface 358 of the baseplate 336. The smooth surface of the first aperture 348 has a length (e.g., along the longitudinal axis of the aperture, left to right on FIG. 9B) and a width (e.g., a diameter or dimension transverse to the longitudinal axis of the aperture, up and down on FIG. 9B). The threaded surface 344 has a length less than or equal to the length of the smooth surface disposed around the central portion 356 of the first aperture. When the threaded surface 344 is housed in the central portion 356, rotation in one direction does not cause the threaded surface 344 and the threads in the aperture 348 to engage each other in a manner permitting advancement along the longitudinal axis of the anchor member 312 or the baseplate 336. For example, if the threaded surface 344 and the threads in the aperture 348 are left-handed, the baseplate 336 can be rotated clockwise without the threads engaging and without the baseplate advancing axially along the longitudinal axis of the anchor member 312. Thus, the anchor member 312 and the baseplate 336 are restrained in axial translation but are permitted to rotate relative to each other.

Of course, the threaded surface 344 and the threads in the aperture 348 could be right-handed and in such arrangement the baseplate could be rotated counterclockwise without the threads engaging.

In some embodiments, the anchor member 312 can be advanced from the distal end 360 of the baseplate 336, through the first aperture 348. The threaded surface 344 of the anchor member 312 can engage the threaded surface 352 of the baseplate 336. The anchor member 312 can be advanced until the threaded surface 344 on the proximal head 340 is proximal of the threaded surface 352 such that the threads of the surface 344 disengage from the threads of the threaded surface 352 of the first aperture 348. When the threaded surface 344 of the proximal head 340 disengages from the threaded surface 352 of the first aperture 348, the threaded surface 344 of the proximal head 340 is disposed within the central portion 356. FIGS. 9A and 9B show that in this configuration, the anchor member 312 is prevented from axial translation with respect to the baseplate 336 but is freely rotatable with respect to the baseplate 336.

In some embodiments, the proximal head 340 of the anchor member 312 is advanced into the central portion 356 of the baseplate 336 before the anchor member 312 is driven into the bone. For instance, the manufacturer can provide the anchor member 312 coupled to the baseplate 336, as shown in FIG. 9A, or this assembly can be provided by the surgeon after selecting the baseplate 336 and/or the anchor member 312 from a plurality of baseplates and/or anchor members as discussed elsewhere herein. The baseplate 336 can be held in a desired orientation when the anchor member 312 is driven into the bone. In some embodiments, the baseplate 336 is maintained in a desired orientation by one or more tools, such as the cannulated tools as described in connection with FIG. 10 below while the anchor member 312 is advanced by rotation into the bone.

According to some methods, the anchor member 312 is partially or fully seated within the bone before the proximal head 340 of the anchor member 312 is advanced into the central portion 356 of the baseplate 336. As noted above, the first aperture 348 and the threaded surface 344 of the proximal head 340 can have left-handed threads. The external lateral surface 364 of the anchor member 100 can have right-handed threads. The baseplate 336 can be rotated with respect to the proximal head 340 such that the proximal head 340 advances through the first aperture 348 and is disposed within the central aperture 356 without disengaging the external lateral surface 364 of the anchor member 312 from the bone. Once the threaded surface 344 on the proximal head 340 is contained within the central portion 356, the surgeon can then rotate the baseplate 336 to align the baseplate 336 with anatomical features of the patient. In some embodiments, following proper orientation of the baseplate 336 relative to the patient, the surgeon can fully seat anchor member 312 into the bone. In some embodiments, the locking structure 112, described in greater detail above, can be utilized with anchor member 312 and baseplate 336. The locking structure 112 applies a force to the anchor member 312, which prevents subsequent rotation of the anchor member 312 with respect to the baseplate 336. The locking structure 112 may also apply a force to glenosphere 116, which creates a frictional lock with the baseplate 336. Further details regarding the use of the locking structure and methods of using the anchor member 312 and baseplate 336 are described below.

FIG. 9A shows that the anchor member 312 can be cannulated. The cannulation allows the anchor member 312 to slide over a guide wire during insertion. The use of a guide wire helps to ensure the proper placement of the anchor member 312 within the bone. The anchor members 104, 104A-104E can also be cannulated to facilitate placement.

Figure 9D:
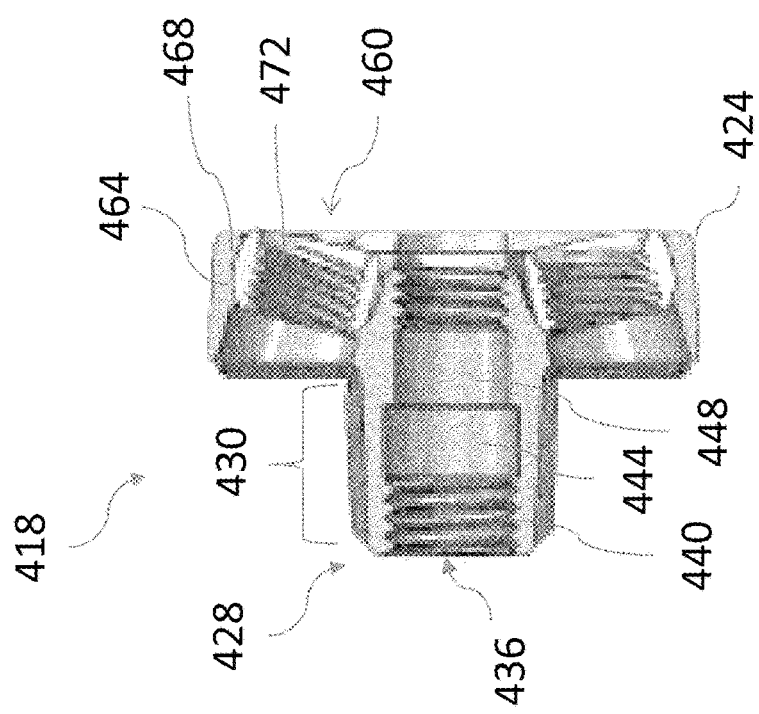
FIG. 9D is a cross-sectional side view of the baseplate of the glenoid implant of FIG. 9C.
Figure 9E:
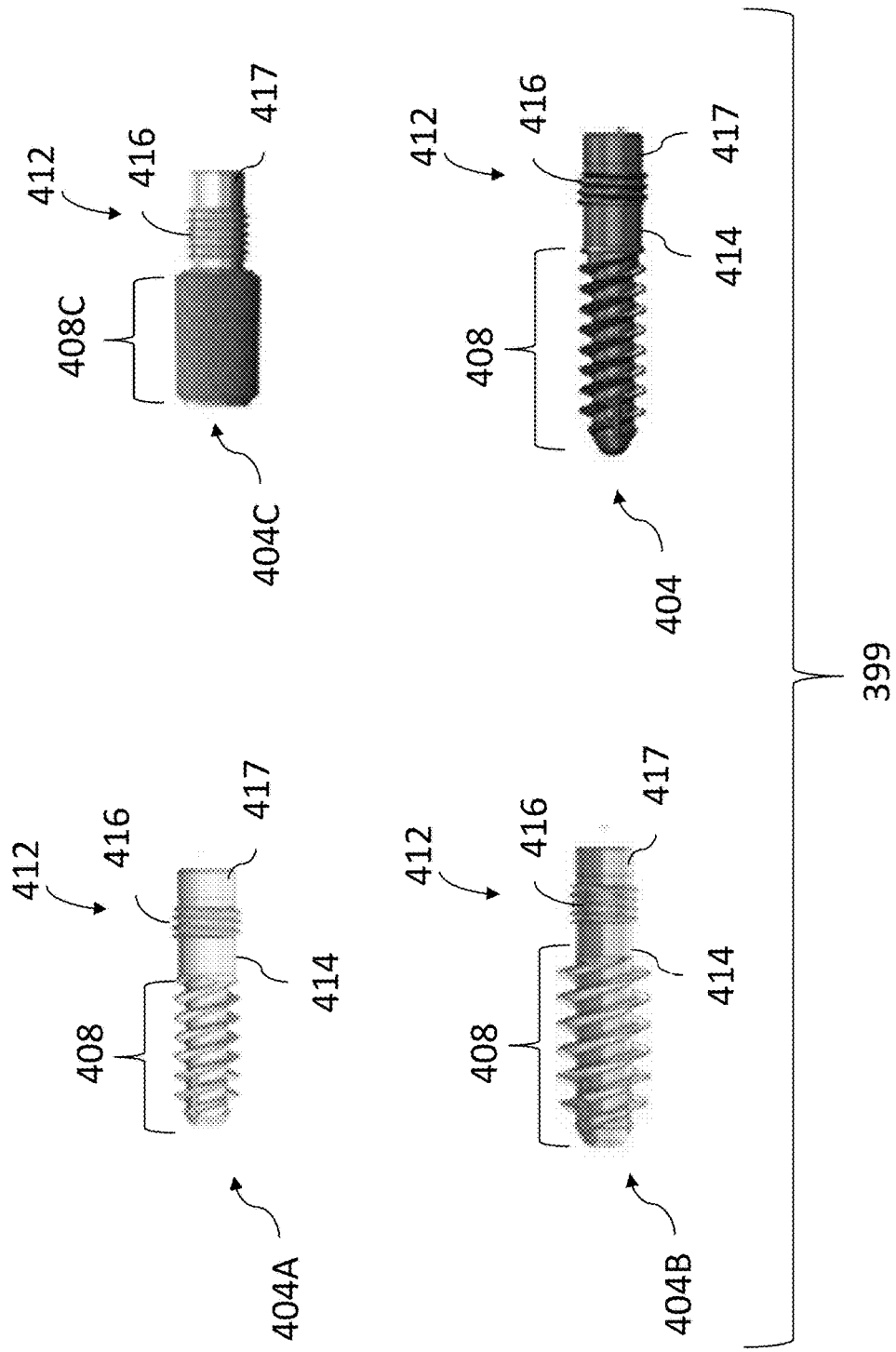
FIG. 9E shows a kit of anchor members, including the anchor member illustrated in FIG. 9C.

FIGS. 9C-9E show an embodiment of a glenoid implant 400 that is similar to the embodiments of FIG. 1 and FIG. 9A except as described differently below. Descriptions of features of the embodiments of FIGS. 1 and 9A-B may be combined singly or in combination with the features of FIGS. 9C-E. The implant 400 is configured to be implanted in a glenoid of a scapula to provide a portion of a shoulder prosthesis. In certain configurations, the implant 400 provides a reverse shoulder component including the glenosphere 116. The glenosphere 116 provides an articulating surface as discussed above.

FIG. 9C shows that the implant 400 includes an anchor member 404. The anchor member 404 is shown in FIGS. 9C and 9E and has a longitudinal portion 408 and a proximal head 412. The proximal head 412 has an external threaded surface 416. The longitudinal portion 408 and the anchor member 404 are configured to be secured to a bone, e.g., into the scapula at the glenoid. In some embodiments, anchor member 404 can be a bone screw component of the implant 400.

FIG. 9E shows that in the anchor member 404 (lower right hand member of the kit 399), the proximal head 412 can include a first smooth portion 414 disposed distally of the external threaded surface 416 and a second smooth portion 417 disposed proximally of the external threaded surface 416. When assembled, the proximal smooth portion 417 can extend between the physical proximal end (articulating surface) of anchor member 404 and the proximal end of the external threaded surface 416. In some cases, the proximal smooth portion 417 can extend entirely from the proximal end of the anchor member 404 to the external threaded surface 416. The distal smooth portion 414 can extend between the external threaded surface 416 and threads disposed on the longitudinal portion 408. The distal smooth portion 414 can extend entirely from the external threaded surface 416 to the threads disposed on the longitudinal portion 408. The proximal smooth portion 417 provides an axial insertion zone that is useful in aligning the threads of the external threaded surface 416 with corresponding mating threads of the implant 400 as discussed further below. The distal smooth portion 414 is adapted to be aligned with, e.g., at the same longitudinal position as, threads of a baseplate 418 of the implant 400 in a configuration that permits axial restraint of the anchor member 404 while permitting rotational orientation of the baseplate 418 as discussed further below.

The baseplate 418 that can be similar to any of the baseplates described herein. FIG. 9D shows an example of the baseplate 418 in more detail. The baseplate 418 can include a proximal end 424 and a distal end 428. A protrusion 430 can be disposed on the distal side of the baseplate 418. The protrusion 430 can be a central protrusion or can be located peripherally as described herein in connection with certain embodiments. The distal end 428 can include a first aperture 436 sized to accept the proximal head 412 of the anchor member 404. The first aperture 436 can comprise an internal threaded surface 440 and a smooth surface 444 disposed therein. The smooth surface can be located proximal of the internal threaded surface 440.

The smooth surface 444 is disposed in the central protrusion 430 at a location immediately adjacent to the threaded surface 440 in one embodiment. The smooth surface 444 defines a portion that permits rotational orienting of the baseplate 418 relative to the anchor member 404 without axially advancing the baseplate 418 relative to an anchor member. The smooth surface 444 can define a length of the first aperture 436 that has a larger diameter than that of the threaded surface 440. The larger diameter section can correspond to a reduced wall thickness radially outward of the smooth surface 444 in the central protrusion 430. In other embodiments, the central protrusion 430 could be thicker in the area of the smooth surface 444 to allow the wall thickness to not decrease in the area of the smooth surface 444. The length of the smooth surface 444 preferably is larger than the length of the external threaded surface 416 of the proximal head 412 of the anchor member 404. As a result, the external threaded surface 416 can be aligned with, e.g., disposed within the smooth surface 444 in one configuration.

The central protrusion 430 preferably also has an anchor member interface zone 448 proximal of the smooth surface 444. The interface zone 448 surrounds the proximal smooth portion 417 of the anchor member 404 in one configuration. The proximal smooth portion 417 can be used to initially align the anchor member 404 with the baseplate 418. For example, the proximal smooth portion 417 can include an unthreaded length that can have an outer diameter that is less than the inner diameter of the threads of the internal threaded surface 440 of the baseplate 418. This permits the unthreaded length of the proximal smooth portion 417 to be inserted into the first aperture 436 and through the internal threaded surface 440 without any threaded engagement. The unthreaded engagement allows the surgeon to align the longitudinal axis of the anchor member 404 with the longitudinal axis of the aperture 436 or otherwise position the anchor member relative to the baseplate 418 to allow for quick threading of the member 404 to the baseplate 418. Such alignment facilitates engaging thread-start(s) of the internal threaded surface 440 with the thread start(s) on the external threaded surface 416 of the anchor member 404 without cross-threading these components. In this context, a thread-"start" is a broad term that includes either end of a thread regardless of whether the end is initially threaded into another structure.

In use, the arrangement of the implant 400 provides for axially restraining the position of the baseplate 418 relative to the anchor member 404. At the same time, the implant 400 permits rotational positioning of the baseplate 418 relative to the anchor member 404. For example, when the external threaded surface 416 of the proximal head 412 is disposed proximal of the internal threaded surface 440 of the first aperture 436, the threads disposed on these threaded surfaces are disengaged. In the illustrated arrangement, the external threaded surface 416 is disposed adjacent to, e.g., in the same longitudinal position within the aperture 436 as the smooth surface 444 of the first aperture 436. In this position, the baseplate 418 is axially restrained but is configured to allow rotational alignment. In this context, the threads are said to be in the same longitudinal position along the longitudinal axis of the aperture 436 when the distal-most aspect of the external threaded surface 416 the anchor member 404 is located proximal of a distal end of the smooth surface 444 of the first aperture 436. In some embodiments, the proximal-most aspect of the external threaded surface 416 of the anchor member 404 is located distal of the proximal end of the smooth surface 444 when the threaded surface 416 is in the same longitudinal position as the surface 444. In some configurations, the distal-most aspect of the external threaded surface 416 is proximal of the distal end of the smooth surface 444 and the proximal-most aspect of the external threaded surface 416 is distal of the proximal end of the smooth surface 444. When the external threaded surface 416 is in the same longitudinal position as the smooth surface 444 there is no thread engagement and thus the threads do not result in axially advancement of the baseplate 418 relative to the anchor member 404 upon relative rotation.

Figure 9F:
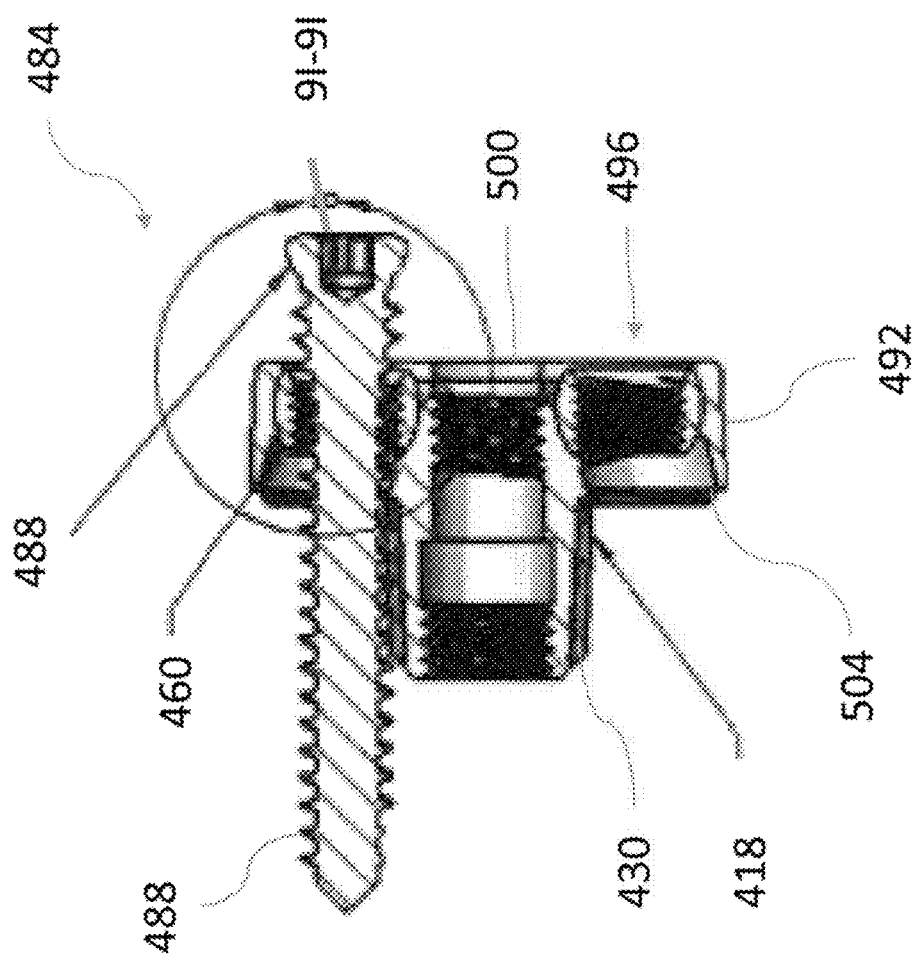
FIG. 9F is a side cross-sectional view of an assembly including the baseplate of FIG. 9D and a peripheral screw.
Figure 9G:
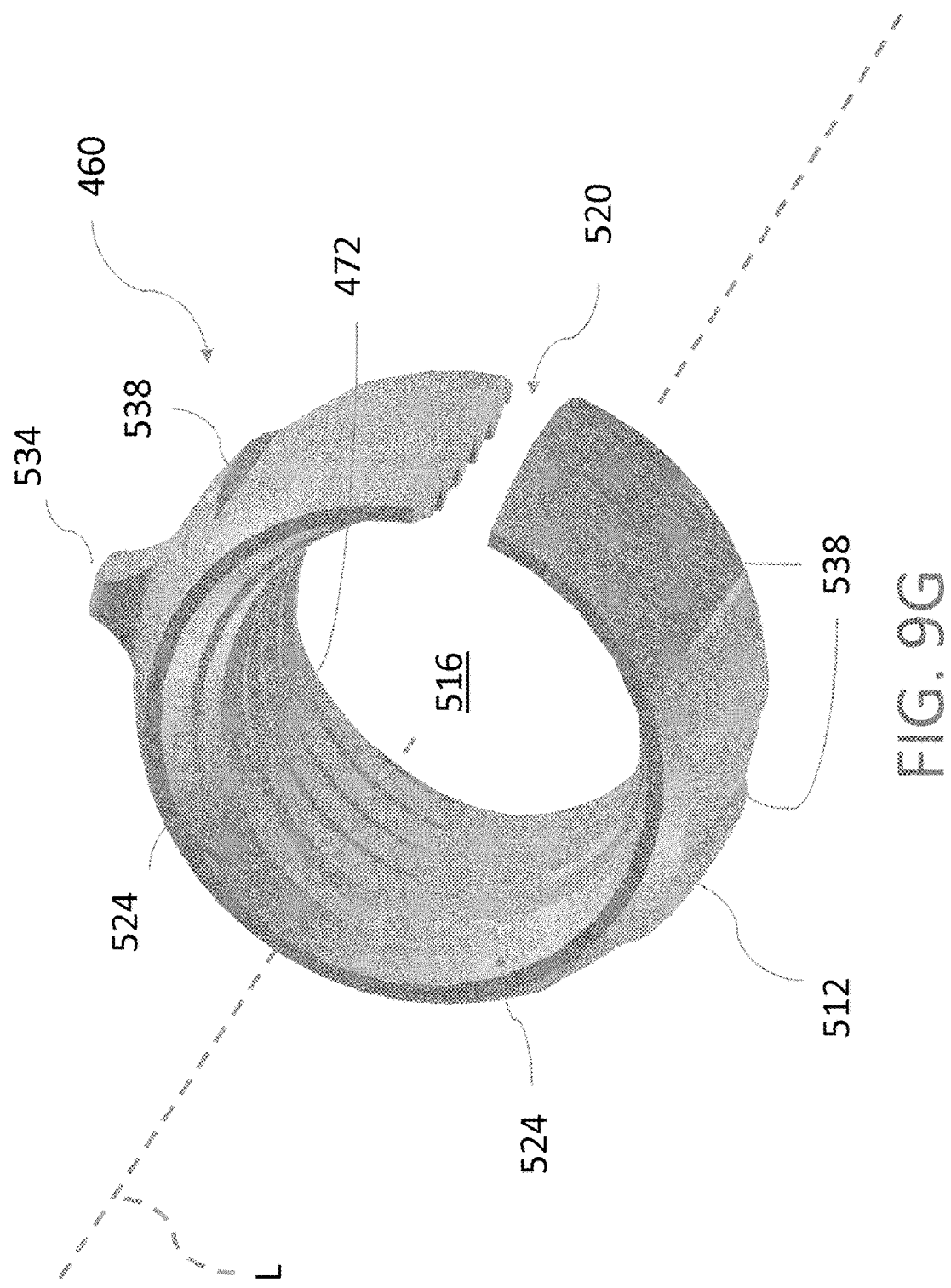
FIG. 9G is a perspective view of one embodiment of an internal member of the baseplate of FIG. 9D.
Figure 9H:
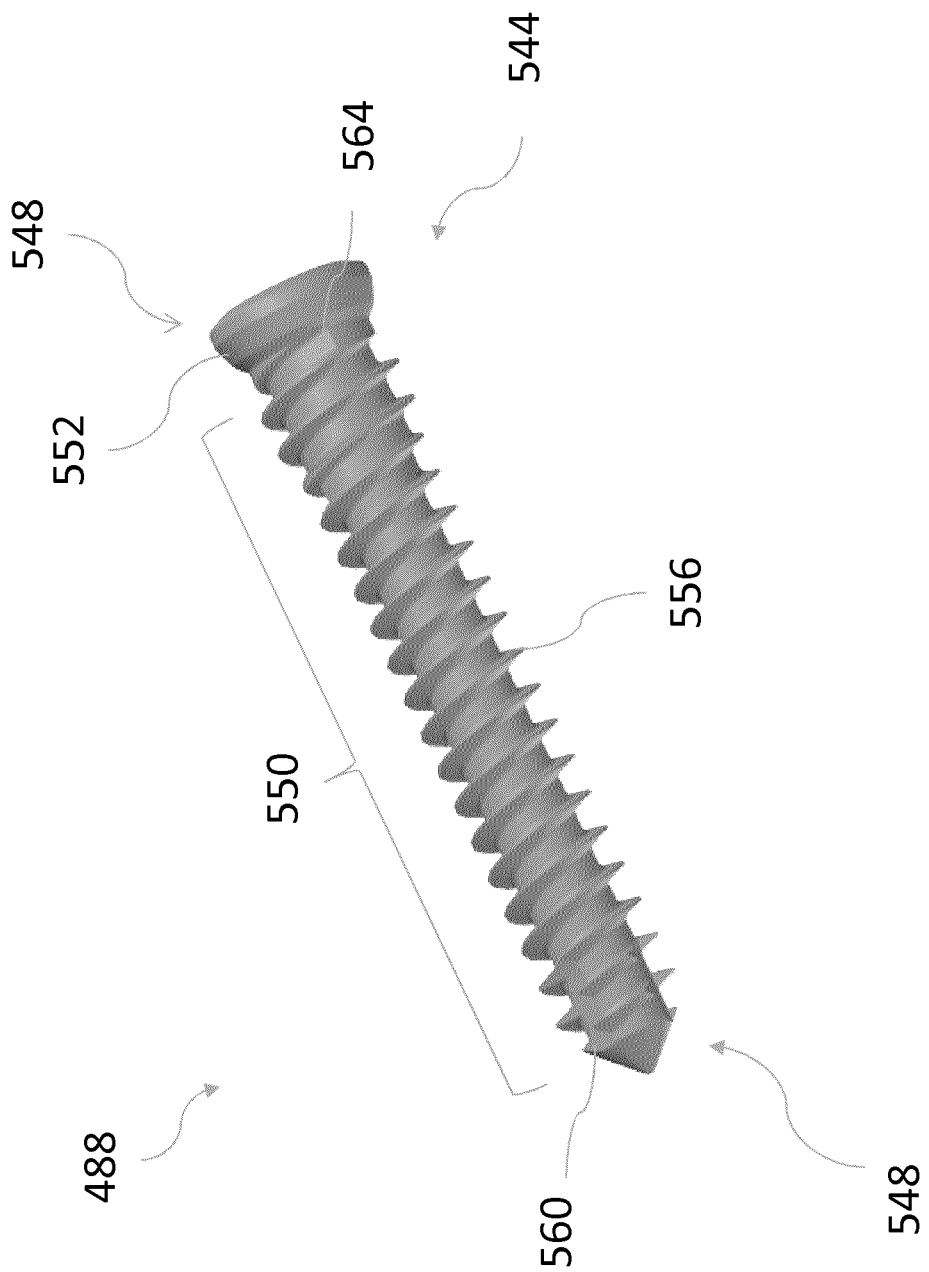
FIG. 9H is a perspective view of one embodiment of a peripheral screw of the glenoid assembly of FIG. 9C.
Figure 91:
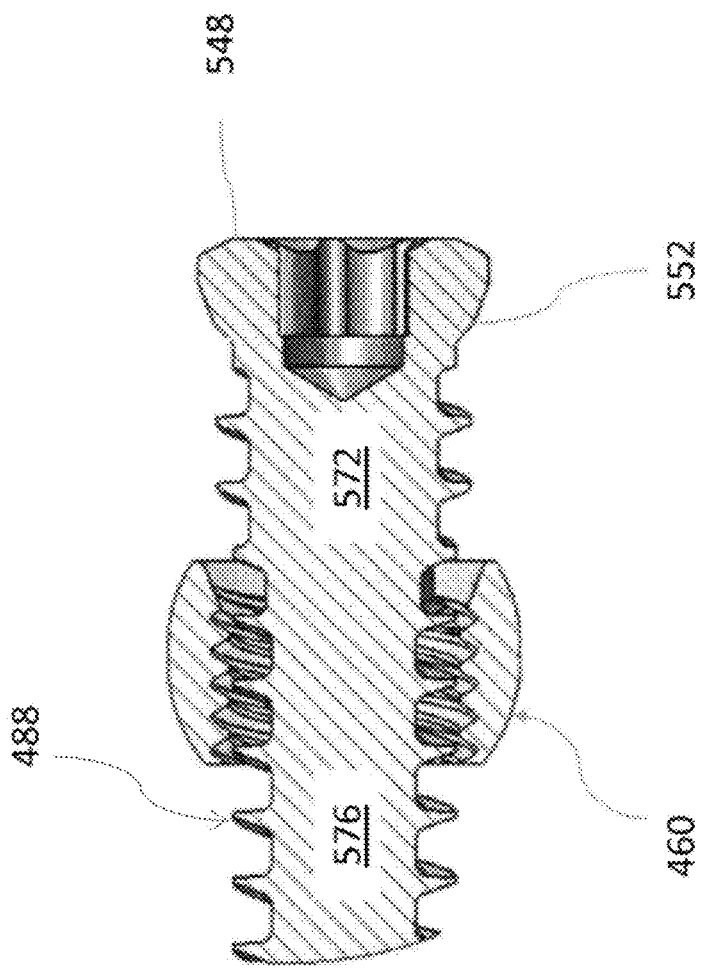

The baseplate 418 also includes an internal member 460 disposed therein. The internal member 460 is disposed peripherally relative to the first aperture 436. The internal member 460 is moveably mounted in the baseplate 418. For example, the internal member 460 can have a spherical outer surface 464 that is mated with a spherical inner surface 468 disposed in the baseplate 418. As discussed below, the internal member 460 can have various flats or projections as well as an outer surface that otherwise generally conforms to a sphere in at least one embodiment. In other embodiments, the internal member 460 has a curved surface that is moveable within the baseplate 418 about a range of motion enabling directing peripheral screws (e.g., the peripheral screw 196 discussed above in connection with FIG. 6) into the bone. The internal member 460 can have internal threads 472 that mate with the peripheral screw. FIGS. 9F-9H, which are discussed below, elaborate on the peripheral screws and internal member 460 provide advantageous features discussed below.

FIG. 9E also shows a kit 399 that can include the anchor member 404 as well as anchor members 404A and 404B having different length and diameter respectively. The anchor member 404A may be well suited for patients with thinner bone portions beneath the glenoid. The anchor member 404B may be well suited for a revision patient, e.g., a patient being adapted from an anatomical shoulder joint to a reverse shoulder joint, where a pre-existing hole in the scapula can be re-used with a larger diameter screw. In each case, the proximal portion of the anchor member 404A, 404B is adapted for the same engagement with a baseplate as described above. That is the smooth sections 414, 417, where provided, can be received in the baseplate 418 and the threaded portion 416 can be disposed in the same longitudinal position in the aperture 436 as the portion 444 to permit rotation of the baseplate relative to the anchors 404A, 404B which rotation does not cause axial advancement of the baseplate as in a threaded connection. An anchor member 404C can be provided with a threadless distal portion. Such an implant can be used to secure in bone where ingrowth provides sufficient securement to the patient's bone or where the bone is too brittle to support a threaded anchor member. The anchor member 404C provides the threaded section 416 immediately adjacent to the distal portion thereof. As a result, the anchor member 404C is able to secure to any of the baseplates herein by virtue of the threads 416. When the threads 416 of the anchor member 404C are fully engaged with a baseplate, further rotation of the baseplate relative to the anchor member 404C will be prevented by the proximal face of the threadless longitudinal portion 408C. Further rotation of a baseplate will result in rotation of the anchor member 404C in the bone. Such further rotation is acceptable because the longitudinal portion 408C is not threaded and thus is not secured to the bone at this stage of the procedure. The anchor member 404C is suitable where less precision is required in rotation alignment of the corresponding baseplate.

A method of using the glenoid implant 100 can include a plurality of steps, in addition to the method of assembling the glenoid implant 100 described above. The surgeon may select one or more of the plurality of steps. Further, a manufacturer providing a glenoid implant can provide instructions for one or more of the plurality of steps.

In one embodiment, a method of using a glenoid implant comprises selecting a preferred baseplate and/or preferred anchor member from a plurality of anchor members such as anchor members 104, 104A-104E, 312 and/or a plurality of baseplates such as baseplates 108, 108B-108G, 336 described above, to best suit the patient. For example, any of the baseplates 108, 108B-108G, 336 and/or the anchors 104, 104A-104E, 312 can be selected based upon the shape of the prepared bone. The baseplates and/or anchors can also be selected based on patient anatomy. For example, a baseplate could be selected that has holes arranged to be positioned above underlying scapular bone. Or a baseplate could be selected that has holes arranged to be positioned above underlying high quality, e.g., high density, bone. As discussed above with reference to FIGS. 5 and 8A-8G, the baseplate can have a variety of different bone engaging surfaces 152, 316, 320, 324 332, and configurations in order to best suit the patient. Further, the surgeon may select from a variety of bone anchors, such as those shown in FIGS. 6, 7A-7E, and 9A-9B. The plurality of anchor members can include different diameters of the longitudinal portion, wherein the bone anchor is selected based on the best fit with the anatomic structure of the patient, specifically the best fit in accordance with the glenoid that was removed. As noted above, the bottom loaded design (e.g., where the anchor member is inserted in the distal end 140 of the baseplate) permits the longitudinal portion and the external lateral surface of the anchor member to have a larger diameter than the diameter of one or more of the following: the second aperture, the first aperture, the lumen, and the central protrusion, which is an advantage for revision cases where much glenoid bone is typically removed. Further, the surgeon can make this selection after exposing the shoulder joint and inspecting the patient's anatomy. The bone anchors in the kit can have different thread pitch, lengths and diameters of the longitudinal portion, and integral components such as those to promote bony ingrowth, as shown in FIG. 7D.

After selecting a preferred anchor member and a preferred baseplate, the surgeon or other practitioner may attach the anchor member to the baseplate. For example, a surgeon may insert the proximal head 220 of any of the anchor members 104, 104A-104E into the first aperture 168 of any of the baseplates 108, 108B-108G. This insertion can result in coupling the anchor member 104, 104A-104E to the baseplate 108, 108B-108G. The proximal head 220 is inserted from the distal end 140 of the baseplate 108, 108B-108G into the first aperture 168. The proximal head 220 does not traverse the second aperture 176. The longitudinal portion 216, 216A-216E of the anchor member 104, 104A-104E remains distal to the baseplate 108, 108B-108G when the proximal head 220 of the anchor member 104, 104A-104E is inserted into the first aperture 168 of the baseplate 108, 108B-108G. The longitudinal portion 216, 216A-216E of the anchor member 104, 104A-104E is not inserted into the first aperture 168. The longitudinal portion 216, 216A-216E of the anchor member 104, 104A-104E is not inserted into the second aperture 176. The longitudinal portion 216, 216A-216E of the anchor member 104, 104A-104E remains outside the confines of the baseplate 108, 108B-108G during coupling of the anchor member 104, 104A-104E to the baseplate 108, 108B-108G. During coupling, the longitudinal portion 216, 216A-216E extends distally.

Figure 10:
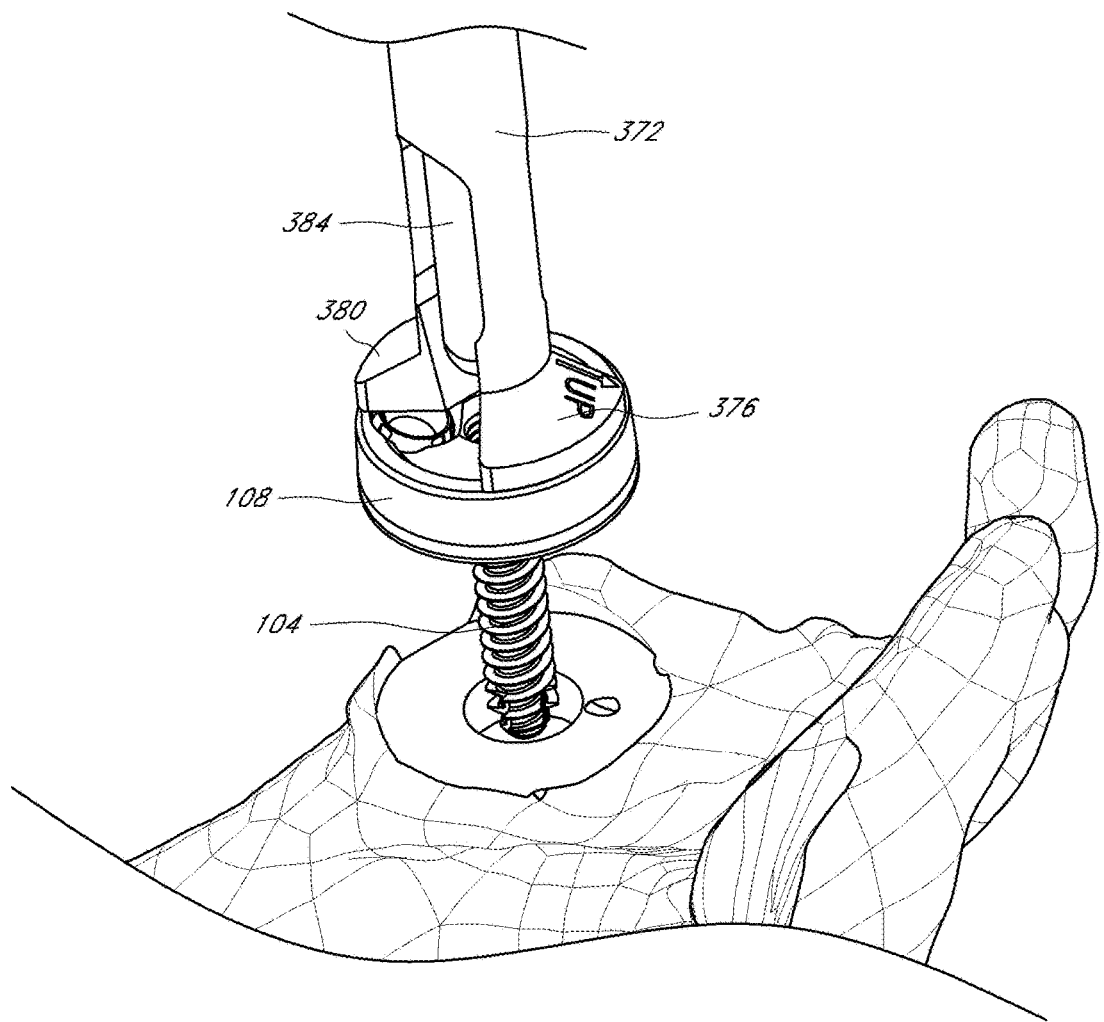
FIG. 10 illustrates an implantation tool and a method of using such a tool to implant a portion of a glenoid implant.

As shown in FIG. 10, an anchor member (such as anchor member 104) with a baseplate pre-attached (such as baseplate 108) can be inserted into a bone such as the scapular glenoid. It will be appreciated that although certain embodiments described herein involve the surgeon or practitioner pre-attaching the anchor member and baseplate before inserting the anchor member into bone, in other embodiments, the anchor member may be inserted separately from the baseplate. For example, an anchor member 104 may be at least partially seated or fully seated within the bone before the proximal head 220 of the anchor member 104 is inserted into the first aperture 168 of the baseplate 108. In yet other embodiments, an anchor member and a baseplate may come pre-attached by the manufacturer.

With reference to FIG. 10, as the surgeon prepares the patient for the implantation of the glenoid implant 100, the surgeon first pierces a hole in the glenoid, typically the hole being slightly smaller than the diameter of the anchor member 104. In one embodiment, the surgeon rotates the anchor member 104 into the glenoid using a tool designed to mate with the cavity 228 of the anchor member, e.g., with a hexagonal tip. This tool may be inserted through the lumen 180 in the baseplate when the baseplate is pre-attached to the anchor member. The self-tapping threads of the external lateral surface 224 of the anchor member 104, if provided, permit the anchor member to be driven into the bone, optionally into the pre-formed hole. The surgeon can insert a guide wire into the bone in combination with a cannulated anchor member. The guide wire can facilitate placement of the anchor member with respect to the bone.

In some methods, a hole is made in the glenoid of a diameter of the central protrusion 160 of the baseplate 108 in order to accommodate the central protrusion 160 when the anchor member is fully seated in the bone. One method step includes shaping the bone to match the distal surface 148 of the baseplate 108. The hole in the glenoid and the shaping of the bone may be done to accommodate the shapes of any of the other baseplates (e.g., baseplates 108B-108G and 336) described herein.

In certain embodiments the anchor member is pre-attached to the baseplate. In other embodiments, the anchor member is or can be attached to the baseplate by the surgeon during implantation.

After advancing the anchor into the bone such that the baseplate is adjacent to the glenoid the anchor member can be rotated (e.g. driven into the bone) without corresponding rotation of the baseplate. These arrangements allow the surgeon to position the baseplate relative to bone, specifically anatomical features of the bone, and maintain that position as the bone anchor member is rotated further into the bone to frictionally secure the baseplate to the bone). In some embodiments, the baseplate 108 is held in a desired orientation when the anchor member 104 is driven into the bone. In some embodiments, the baseplate 108 is maintained in a desired orientation by tools, as described below.

Referring now to FIG. 10, in some methods tools are used to maintain the orientation of the baseplate 108 relative to the bone. In one embodiment, a cannula 372 is configured to interact with the baseplate 108. In some embodiments, the cannula 372 has two radially extending legs 376, 380. The radially extending legs 376, 380 permit the cannula 372 to be a smaller diameter than the diameter of the baseplate 108. In some embodiments, the radially extending legs 376, 380 include a distal feature that mates with a feature on the proximal end 136 of the baseplate 108, for instance with tool engaging grooves 398 shown in FIG. 8A. In some embodiments, the radially extending legs 376, 380 may extend, and partially cover the holes 188, 192. In some embodiments, the cannula 372 is sized to accept an inner cannula 384. The inner cannula 384 can have multiple functions in some embodiments. The inner cannula 384 can be configured to assist in docking and un-docking the legs 376, 380 with the baseplate 108. For example, the outer profile of the inner cannula 384 can be larger than the inner profile of the outer cannula 372 near the distal end of the legs 376, 380. As the inner cannula 384 is advanced distally in the outer cannula 372 the outer surface of the inner cannula 384 spreads the legs 376, 380. Another function for the inner cannula 384 in some embodiments is to provide access for a driver therethrough to mate with the cavity 228 in the proximal head 220 of the anchor member 104. The inner cannula 284 can have an inner lumen to provide such access. Thus, the driver can be used to insert the anchor member 104 into the bone while the cannula 372 maintains the rotational orientation of the baseplate 108. The cannula 372 may further be used to rotate baseplate 108 to a desired orientation with respect to the bone.

In some embodiments, the baseplate 108 is rotated to align the holes 188, 192 (shown in FIG. 6) with anatomic features of the patient. In some embodiments, the baseplate 108 is rotated to align the bone engaging surface 152 with anatomic features of the patient. When the baseplate 108 is coupled to the anchor member 104, the baseplate 108 is freely rotatable with respect to the anchor member 104. The baseplate 108 can be rotated and orientated without adjusting the rotational position of the anchor member 104. The anchor member 104 can be rotated and orientated without adjusting the rotational position of the baseplate 108. In some embodiments, the baseplate 108 is rotated after the anchor member 104 is partially or fully driven into the bone. In some embodiments, the baseplate 108 is rotated before the anchor member 104 is driven into the bone.

Following proper orientation of the baseplate 108 relative to the bone, the surgeon can fully seat anchor member 104 into the bone using the driver. After the anchor member 104 is fully seated in the bone and the baseplate 108 is properly oriented relative to the bone, or peripheral anchors or screws 196 such as shown in FIG. 6 may be inserted into holes 188 and 192 provided in the baseplate 108. In some embodiments, perimeter anchors 196 are inserted from the proximal end 136 of the baseplate 108 to the bone engaging surface 152 of the baseplate 108, or through the baseplate 108. This is the opposite direction the anchor member 104 is inserted into the baseplate 108.

FIGS. 9F-9J show variations of an advantageous peripheral screw assembly 484 of the glenoid implant 400. The peripheral screw assembly 484 includes the baseplate 418, an internal member 460 and a peripheral screw 488. The internal member 460 is disposed between an outer periphery 492 of the baseplate 418 and the central protrusion 430.

FIG. 9F shows an aperture 496 that extends through the baseplate 418 adjacent to the outer periphery 492. The aperture 496 extends from a proximal surface 500 of the baseplate 418 to a distal portion 504 thereof. The distal portion 504 can be a side of the baseplate 418 that engages the bone when the baseplate 418 is applied to the patient. In FIG. 9F one of the apertures 496 is labeled and another aperture 496 is shown with a peripheral screw 488 disposed therein, but not labeled for clarity. The internal member 460 is disposed in the aperture 496 of the baseplate 418. FIG. 9G shows the internal member 460 having an internal threaded surface 472. The internal threaded surface 472 is disposed within the aperture 496.

FIG. 9G shows that in one embodiment, the internal member 460 has a C-shaped configuration including a peripheral wall 512. The peripheral wall 512 extends around a lumen 516. The lumen 516 extends along an axis L. A gap 520 is provided in the wall 512. The gap 520 provides for flexing and movement of the internal member 460 when disposed in the baseplate 418. The outer surface 520 of the wall is configured to permit rotation of the internal member 460 within the aperture 496. For example, the outer surface can be curved and even at least partially spherical in some embodiments to move easily in the aperture 496 prior to being secured into a selected orientation as discussed below. The internal threaded surface 472 has a thread-start 524 disposed thereon. As discussed above, in this context, a thread-"start" is a broad term that includes either end of a thread regardless of whether the end is initially threaded into another structure. In some embodiments, the internal threaded surface 472 has a plurality of thread-starts 524 disposed therein. FIG. 9G shows an embodiment with four thread-starts. Two of the thread-starts 524 are shown in the perspective view and an additional two thread-starts are disposed on a portion of the wall opposite to the thread-starts that are shown. In other embodiments, there can be six, eight or ten or any other number of thread-starts.

The internal member 460 can have other features disposed on the outside wall thereof. A protrusion 534 can be disposed on the outside wall to engage a corresponding recess in the aperture 496 of the baseplate. The protrusion 534 allows the internal member 460 to rotate but prevents the member from being dislodged from the aperture 496. The internal member 460 can have flats 438 disposed on the external wall. The flats make the internal member 460 more flexible such that it can be deflected to a secured configuration as discussed below.

The peripheral screw assembly 484 includes the peripheral screw 488 configured to be placed through the aperture 496. The screw 488 has a proximal end 544, a distal end 548, and a body 550 that extends along the length thereof. The proximal end 544 can include a head 548 that has a tool engagement feature on an end and a tapered portion 552 projecting distally from the end. The screw 488 has an external threaded surface 556. The external threaded surface 556 includes a thread-start 560 disposed at the distal end 548. Accordingly, the external threaded surface 556 includes a thread-start 564 disposed near the proximal end 544 adjacent to the tapered portion 552 of the head 548.

FIGS. 9H-9I show that the peripheral screw 488 includes profile with a diameter that is not constant along the length of the body of the screw. The screw 488 has a proximal portion 572 with a larger diameter section and a distal portion 576 with a smaller diameter section. The diameter of the screw 488 is enlarged, and may be stepped or changed in diameter in some embodiments adjacent to the proximal end 544 of the screw 488. The screw 488 preferably has the same thread form in the proximal portion 572 and in the distal portion 576. For example, the thread pitch can be the same in the proximal and distal portions 572, 576. The constant thread form in combination with the threading of internal member 460 enables the screw 488 to be advanced at a constant rate in both the proximal and distal portions 572, 576.

In one embodiment, the internal member 460 has a first number of thread-starts 524 disposed on the internal threaded surface 472. The number of thread-starts is greater than the number of thread-starts on the disposed on the external threaded surface 556 of the anchor member 488. This enables the screw 488 to be more rapidly advanced through the internal member 460. In one embodiment, the glenoid implant 400 is provided with the internal member 460 having two times the number of thread-starts 524 as the number of thread-starts 560 on the anchor member 488.

FIG. 9I shows partial advancement of the peripheral screw 488 through the internal member 460. In this position, the gap 520 of the member 460 is not significantly expanded by the presence of the screw. As a result, the internal member is permitted to move to some extent allowing the trajectory of the aperture 496 and accordingly the screw 488 to be adjusted relative to the baseplate.

Figure 9J:
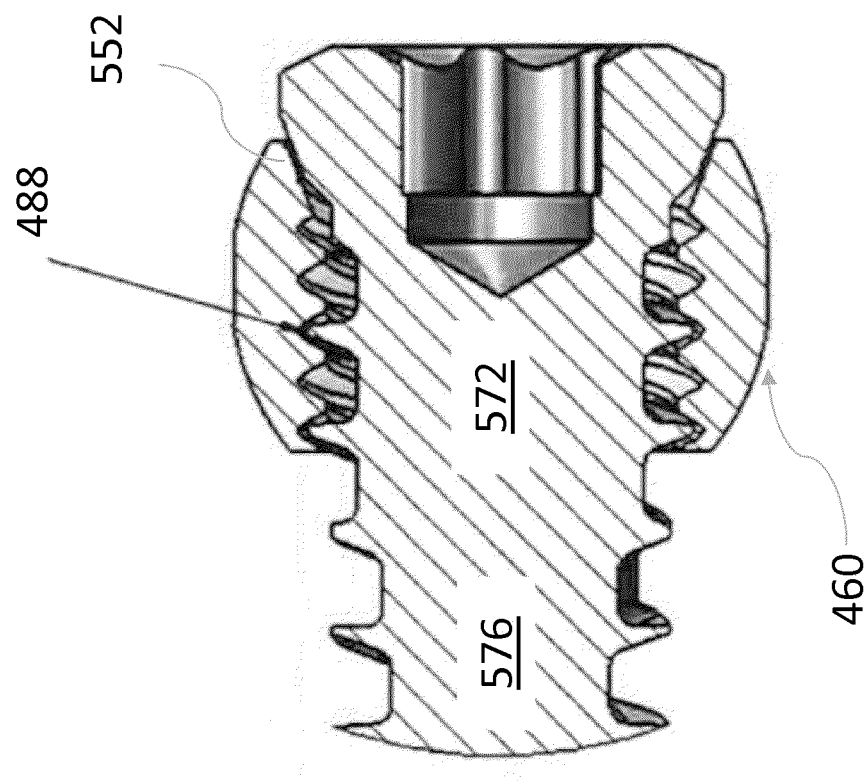
FIG. 9J is a side cross-sectional view of the proximal portion of the peripheral screw of FIG. 9H fully advanced through the internal member of FIG. 9G.

FIG. 9J shows full advancement of the peripheral screw 488 through the internal member 460. In this position, the proximal portion 572 is disposed within the internal member 460. The larger diameter of the proximal portion 572 causes the internal member 460 to expand within the aperture 496. When the screw 488 is in this position, the gap 520 is enlarged to an extent sufficient to cause the peripheral wall 512 to be urged into secure engagement with an inside of the baseplate 418. The secure engagement can include a high friction force being applied between these walls of the implant 400 such that movement of the aperture 496 is not possible or is minimal. By securing the orientation of the internal member 460 there is less play in the implant 400 making the implant less prone loosening after being secured to the scapula.

In some embodiments, after the anchor member and baseplate are attached to the bone, the locking structure 112 may be used to further secure the anchor member relative to the baseplate and to attach the glenosphere to the baseplate. For example, after the anchor member 104 shown in FIG. 10 has been inserted into the bone, the baseplate 108 is in the desired orientation with respect to the patient, and the perimeter anchors 196 have been inserted, the rotation of the anchor member 104 with respect to the baseplate 108 can be restricted via the locking structure 112. With the locking structure 112 already assembled as described with respect to FIG. 3 above, and either with or without the glenosphere 116 attached to the threaded member 264, the locking screw 256 is inserted into the second aperture 176 of the baseplate which has the threaded surface 184. The locking screw 256 is rotated until the locking screw 256 applies a force on the proximal head 220 of the anchor member 104. In some embodiments, the locking screw 256 enters a cavity 228 in the proximal head 220 of the anchor member 104. In some embodiments, the force interacts with the member 240 to prevent rotation of the anchor member 104 with respect to the baseplate 108. After application of force by the locking screw 256, the anchor member 104 is prohibited from axial translation and rotation with respect to the baseplate 108.

With the locking structure 112 in place, a glenosphere 116 such as shown in FIGS. 3 and 4 may be attached to the baseplate 108. In one embodiment, the glenosphere 116 may have already been attached to the threaded member 264 when the locking screw 256 is inserted into the cavity 228 in the proximal head 220 of the anchor member 104. In another embodiment, the glenosphere 116 may be attached to threaded member 264 after the locking screw 256 is inserted into the cavity 228. In some embodiments, the lateral surface 156 of the baseplate 108 is tapered and the interior surface 248 of the glenosphere 116 is tapered. When the glenosphere 116 moves distally, the interior surface 248 engages with the lateral surface 156 of the baseplate 108. In some embodiments, the interior surface 248 and the lateral surface 156 form a Morse taper.

In some embodiments, the locking screw 256 simultaneously applies a force to the anchor member 104 and the glenosphere 116 when the locking screw 256 is advanced through the second aperture 176. In some embodiments, the glenoid implant 100 is dimensioned so that the locking screw 256 applies a force to the proximal head 220 of the anchor member 104 simultaneously with the glenosphere 116 interior surface 248 mating with the lateral surface of the baseplate 108. In this way, the locking screw 256 creates a downward force on the anchor member 104 and creates a downward force on the threaded member 264 which is coupled to the glenosphere 116. The downward force causes the interior surface 248 and the lateral surface 156 to engage. In some embodiments, the locking screw 256 creates a push force on the glenosphere 116 and/or a pull force on the baseplate 108.

As illustrated in FIG. 4, the compression washer 260 provided between the proximal head 276 of the locking screw 256 and the baseplate 108 may be utilized to prevent micromotion. The compression washer 260 provides resistance against backout when the locking screw 256 creates a push force on the anchor member 104. The compression washer 260 is designed to fill the space between the proximal head 276 of the locking screw 256 and the threaded member 264 as the locking screw 256 creates a push force on the glenosphere 116 and/or pull force on the baseplate 108. The placement and use of the compression washer 260 facilitates the rigidity of the glenoid implant 100, and further prevents rotation, translation and/or micromotion of the anchor member 104 with respect to the baseplate 108. Further, preventing micromotion involves no additional step from the current procedure of securing a locking member.

In some embodiments, a bone graft (not shown) may be placed into the bone. The bone graft can be attached to or disposed about any of the surfaces or portions of the baseplates described herein including the distal surface 148, distal end 140, the bone engaging surface 152, 316, 320, 324, 332, the central protrusion 160, 328, or the longitudinal portion 216, 216A-216E of the anchor member 104, 104A-104E or any other feature that would benefit from bony ingrowth. Allowing the anchor member 104, 104A-104E to be driven into the bone independently of rotation of the baseplate 108, 108B-108G causes less wear and stress on the bone graft during insertion. In some embodiments, the anchor member 104, 104A-104E is freely rotatable with respect to the bone graft. In some embodiments, the bone graft is coupled to the baseplate 108, 108B-108G and rotates when the baseplate 108, 108B-108G rotates but not when the anchor member 104, 104A-104E rotates. In some embodiments, the bone graft is inserted after the anchor members 104, 104A-104E is fully or partially seated within the bone.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A method of using a glenoid implant for a shoulder prosthesis comprising:
    securing an anchor member at least partially to bone, the anchor member comprising a longitudinal portion configured to be secured to a bone and a proximal head, wherein the proximal head has a first engaging surface;
    inserting the proximal head of the anchor member into a baseplate from a distal end of the baseplate, the baseplate further comprising a proximal end and a first aperture sized to accept the proximal head of the anchor member, the first aperture comprising a second engaging surface;
    with the proximal head of the anchor member inserted into the first aperture, coupling the first engaging surface to the second engaging surface such that the proximal head and the baseplate are axially fully connected, and thereafter rotating the baseplate relative to the anchor member to adjust the position of the baseplate without adjusting the rotational position of the anchor member; and
    securing the baseplate to the bone by inserting a perimeter anchor into the bone.

2. The method of claim 1, further comprising, prior to securing the anchor member at least partially to bone, inserting the proximal head into the first aperture to cause the first engaging surface to couple with the second engaging surface.

3. The method of claim 1, further comprising restraining the anchor member against axial translation with respect to the baseplate but permitting rotation of the anchor member with respect to the baseplate when the first engaging surface is coupled to the second engaging surface.

4. The method of claim 3, wherein the first engaging surface and the second engaging surface are structured and configured such that forces exerted between said engaging surfaces substantially restrain the anchor member against axial translation with respect to the baseplate and substantially do not restrain rotation of the anchor member with respect to the baseplate.

5. The method of claim 4, wherein inserting the proximal head into the baseplate further comprises coupling a member to the first engaging surface and the second engaging surface, further wherein said member transmits forces exerted between said engaging surfaces.

6. The method of claim 1, wherein inserting the proximal head into the baseplate further comprises coupling a member to the first engaging surface and the second engaging surface.

7. The method of claim 6, wherein coupling the member to the first engaging surface and the second engaging surface comprises elastically deforming the member as the proximal head is inserted into the baseplate.

8. The method of claim 6, wherein the first engaging surface is a first groove and the second engaging surface is a second groove, and wherein coupling the member to the first engaging surface and the second engaging surface comprises disposing the member in a gap formed when the first groove is longitudinally aligned with the second groove.

9. The method of claim 1, wherein inserting the proximal head into the baseplate further comprises preventing the proximal head from passing from the distal end of the baseplate to the proximal end of the baseplate.

10. The method of claim 1, wherein inserting the proximal head into baseplate further comprises preventing the longitudinal portion from passing from the distal end of the baseplate to the proximal end of the baseplate.

11. The method of claim 1, further comprising locating the longitudinal portion of the anchor member distally to the distal end of the baseplate during the step of inserting the proximal head into the baseplate.

12. The method of claim 1, further comprising applying a force to the anchor member with a locking member to prevent rotation between the anchor member and the baseplate.

13. The method of claim 12, wherein the step of applying a force to the anchor member such that the anchor member is no longer freely rotatable with respect to the baseplate further comprises preventing micromotion.

14. The method of claim 12, further comprising engaging a glenosphere to the baseplate.

15. The method of claim 14, further comprising applying a force to the baseplate such that a third engaging surface on the baseplate between the proximal end and distal end of the baseplate couples with a fourth engaging surface on the glenosphere.

16. The method of claim 1, wherein inserting the perimeter anchor comprises inserting the perimeter anchor from the proximal end of the baseplate to the distal end of the baseplate.

17. The method of claim 16, wherein rotating the baseplate relative to the anchor occurs before inserting the perimeter anchor such that the perimeter anchor engages a target location in the bone.

18. The method of claim 1, wherein the anchor member is secured to a scapula bone.

19. The method of claim 1, wherein the first engaging surface comprises threads disposed on the anchor member and the second engaging surface comprises threads disposed in the first aperture; the method further comprising:
rotating the baseplate relative to the anchor member in a first direction such that the threads in the first aperture engage the threads on the anchor member; and
further rotating the baseplate relative to the anchor member in the first direction such that the threads in the first aperture and the thread on the anchor member disengage, the threads on the anchor member being disposed within the baseplate when disengaged.

20. The method of claim 19, further comprising rotating the baseplate in a second direction opposite the first direction to align the baseplate with high quality underlying bone.

21. The method of claim 1, wherein coupling the first engaging surface to the second engaging surface comprises positioning a means for indirectly coupling the first engaging surface and the second engaging surface in the first aperture.

22. The method of claim 1, wherein coupling the first engaging surface to the second engaging surface comprises positioning a deformable means between the first engaging surface and the second engaging surface.

23. The method of claim 1, wherein the second engaging surface comprises a smooth region longitudinally displaced from the distal end of the baseplate, and wherein coupling the first engaging surface to the second engaging surface comprises disposing the first engaging surface of the proximal head within the smooth region of the second engaging surface.

24. The method of claim 1, wherein the first engaging surface comprises threads disposed on the anchor member and the second engaging surface comprises a threaded region and a smooth region disposed in the first aperture, and wherein coupling the first engaging surface to the second engaging surface comprises:
rotating the baseplate relative to the anchor member such that the threaded region in the first aperture engages the threads on the anchor member; and
further rotating the baseplate relative to the anchor member such that the threads on the anchor member are disposed within the smooth region of the second engaging surface.

25. The method of claim 1, wherein the glenoid implant comprises means for constraining relative motion of the anchor member and the baseplate, such that when the proximal head and the baseplate are axially fully connected, axial translation therebetween is substantially prevented, and the anchor member and baseplate are substantially free to rotate with respect to each other.

26. The method of claim 25, wherein the means for constraining relative motion includes the first engaging surface and the second engaging surface.

27. The method of claim 26, wherein the means for constraining relative motion includes a member coupled to the first engaging surface and the second engaging surface.

28. A method of using a glenoid implant for a shoulder prosthesis comprising:
securing an anchor member at least partially to bone, the anchor member comprising a longitudinal portion configured to be secured to a bone and a proximal head;
inserting the proximal head of the anchor member into a baseplate in a direction perpendicular to a proximal face of the baseplate, the baseplate comprising a proximal end, a distal end, and a first aperture sized to accept the proximal head of the anchor member from the distal end of the baseplate;
restraining the anchor member against axial translation with respect to the baseplate in both directions along a longitudinal axis but permitting rotation of the anchor member with respect to the baseplate; and
securing the baseplate to the bone.

29. The method of claim 28, further comprising preventing the proximal head from passing from the distal end of the baseplate to the proximal end of the baseplate.

30. The method of claim 28, further comprising preventing the longitudinal portion from passing from the distal end of the baseplate to the proximal end of the baseplate.

31. The method of claim 28, further comprising applying a force to the anchor member with a locking member to prevent rotation between the anchor member and the baseplate.

* * * * *

UNITED STATES PATENT AND TRADEMARK OFFICE
CERTIFICATE OF CORRECTION

PATENT NO. : 10,357,373 B2
APPLICATION NO. : 15/474864
DATED : July 23, 2019
INVENTOR(S) : Gargac et al.

It is certified that error appears in the above-identified patent and that said Letters Patent is hereby corrected as shown below:

In the Claims

At Column 28, Line 67, in Claim 10, after "into" add --the--.

Signed and Sealed this
Twenty-ninth Day of October, 2019

Andrei Iancu
*Director of the United States Patent and Trademark Office*